United States Patent
Allegrini et al.

(10) Patent No.: US 10,717,715 B2
(45) Date of Patent: Jul. 21, 2020

(54) SOLID FORMS OF INGENOL 3-(3,5-DIETHYLISOXAZOLE-4-CARBOXYLATE) AND METHOD FOR PREPARING THE SAME

(71) Applicant: INDENA S.P.A., Milan (IT)

(72) Inventors: Pietro Allegrini, Milan (IT); Federico Peterlongo, Milan (IT); Andrea Gambini, Milan (IT); Daniele Ciceri, Milan (IT); Nicola Sardone, Milan (IT); Maurizio Ricotti, Milan (IT)

(73) Assignee: INDENA S.P.A., Milan (IT)

( * ) Notice: Subject to any disclaimer, the term of this patent is extended or adjusted under 35 U.S.C. 154(b) by 0 days.

(21) Appl. No.: 16/330,909

(22) PCT Filed: Aug. 29, 2017

(86) PCT No.: PCT/EP2017/071589
§ 371 (c)(1),
(2) Date: Mar. 6, 2019

(87) PCT Pub. No.: WO2018/046337
PCT Pub. Date: Mar. 15, 2018

(65) Prior Publication Data
US 2019/0210980 A1 Jul. 11, 2019

(30) Foreign Application Priority Data
Sep. 6, 2016 (EP) .................................. 16187316

(51) Int. Cl.
*C07D 261/18* (2006.01)
(52) U.S. Cl.
CPC ........ *C07D 261/18* (2013.01); *C07B 2200/13* (2013.01)
(58) Field of Classification Search
CPC .......................... C07D 261/18; C07B 2200/13

USPC ......................................................... 548/248
See application file for complete search history.

(56) References Cited

FOREIGN PATENT DOCUMENTS

WO 2012/083953 6/2012

OTHER PUBLICATIONS

Byrn et al., Solid-State Chemistry of Drugs, 1999, SSCI, Inc., Second Edition, pp. 62-63 (Year: 1999).*
Newman et al., Solid-state analysis of the active pharmaceutical ingredient in drug products, DDT, vol. 8, No. 19, Oct. 2003, pp. 898-905 (Year: 2003).*
Chawla et al., Challenges in Polymorphism of Pharmaceuticals, CRIPS, vol. 5, No. 1, Jan.-Mar. 2004, pp. 9-12 (Year: 2004).*
Brittain et al., Polymorphism in Pharmaceutical Solids, 1995, vol. 95, p. 228-229 (Year: 1995).*
International Search Report for Application No. PCT/EP2017/071589, dated Jan. 30, 2018.
Lian Yu et al., "Physical characterization of polymorphic drugs: an integrated characterization strategy," Pharmaceutical Science and Technology Today, Elsevier Trends Journals, vol. 1, No. 3, Jun. 1, 1998.

* cited by examiner

*Primary Examiner* — Kristin A Vajda
(74) *Attorney, Agent, or Firm* — Young & Thompson

(57) ABSTRACT

Disclosed are solid forms of ingenol 3-(3,5-diethylisoxazole-4-carboxylate) selected from an amorphous form or a crystalline anhydrous form. Also disclosed are solid solvates of ingenol 3-(3,5-diethylisoxazole-4-carboxylate) selected from an acetone solvate, a dimethylcarbonate solvate, an isopropyl ether solvate, an acetonitrile solvate, a toluene solvate, a mesitylene solvate, a nitromethane solvate, a dichloromethane/heptane solvate and an ethyl acetate solvate, for use as intermediates.

13 Claims, 32 Drawing Sheets

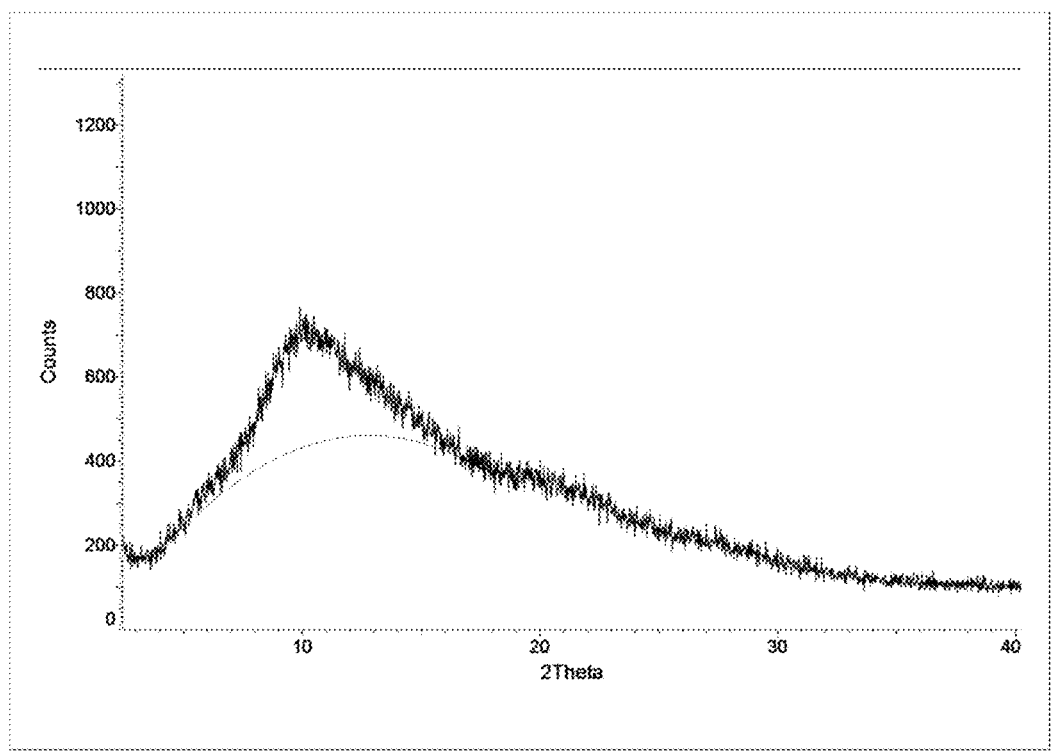
FIG. 1 (XRPD of amorphous ingenol 3-(3,5-diethylisoxazole-4-carboxylate)

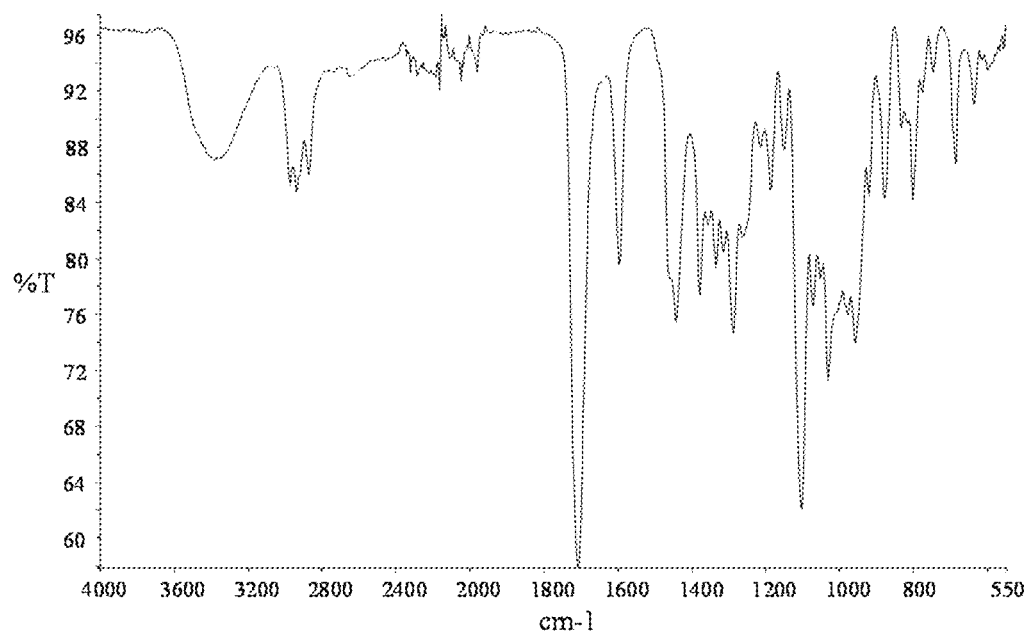
FIG. 2 (FTIR of amorphous ingenol 3-(3,5-diethylisoxazole-4-carboxylate)

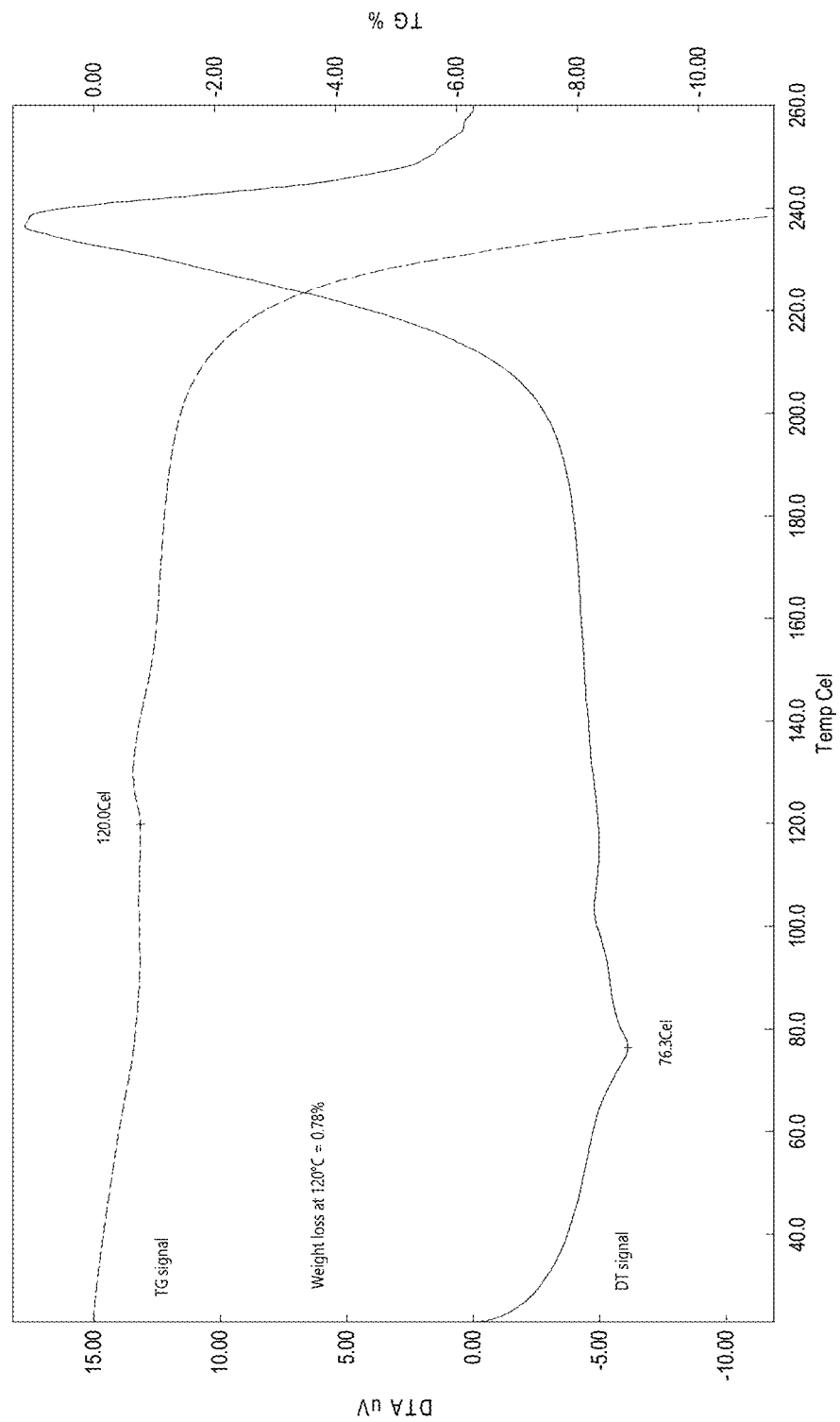
FIG. 3 (TG/DTA of amorphous ingenol 3-(3,5-diethylisoxazole-4-carboxylate)

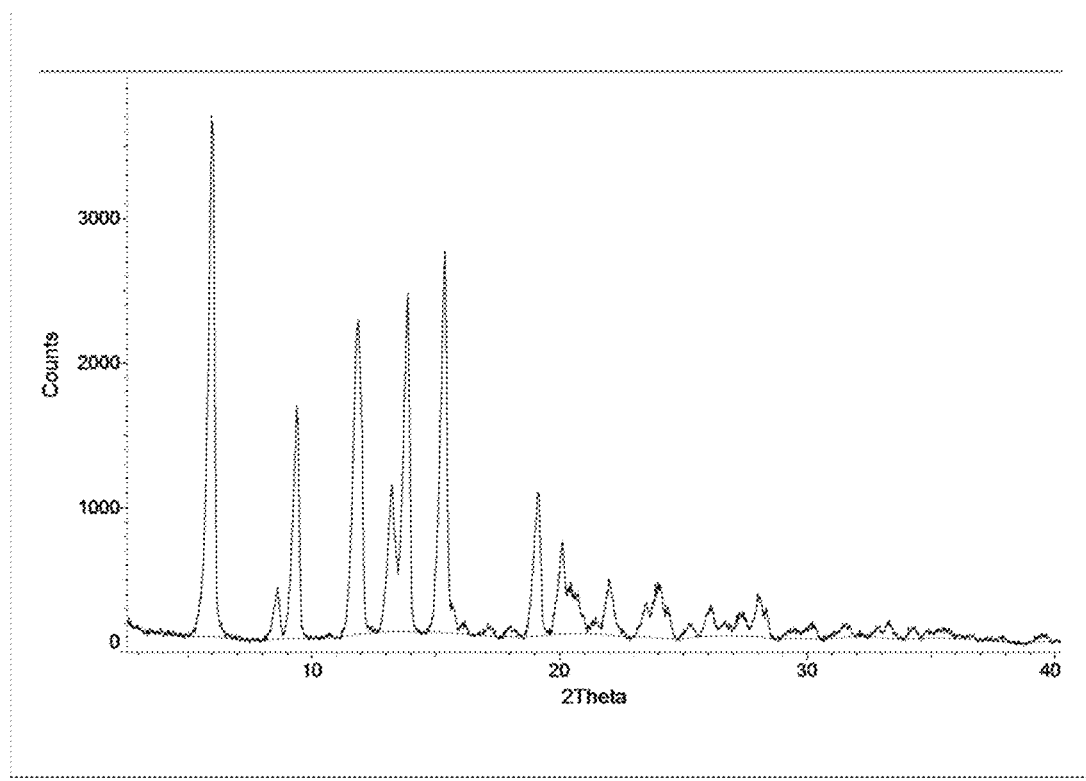
FIG. 4 (XRPD of anhydrous ingenol 3-(3,5-diethylisoxazole-4-carboxylate)

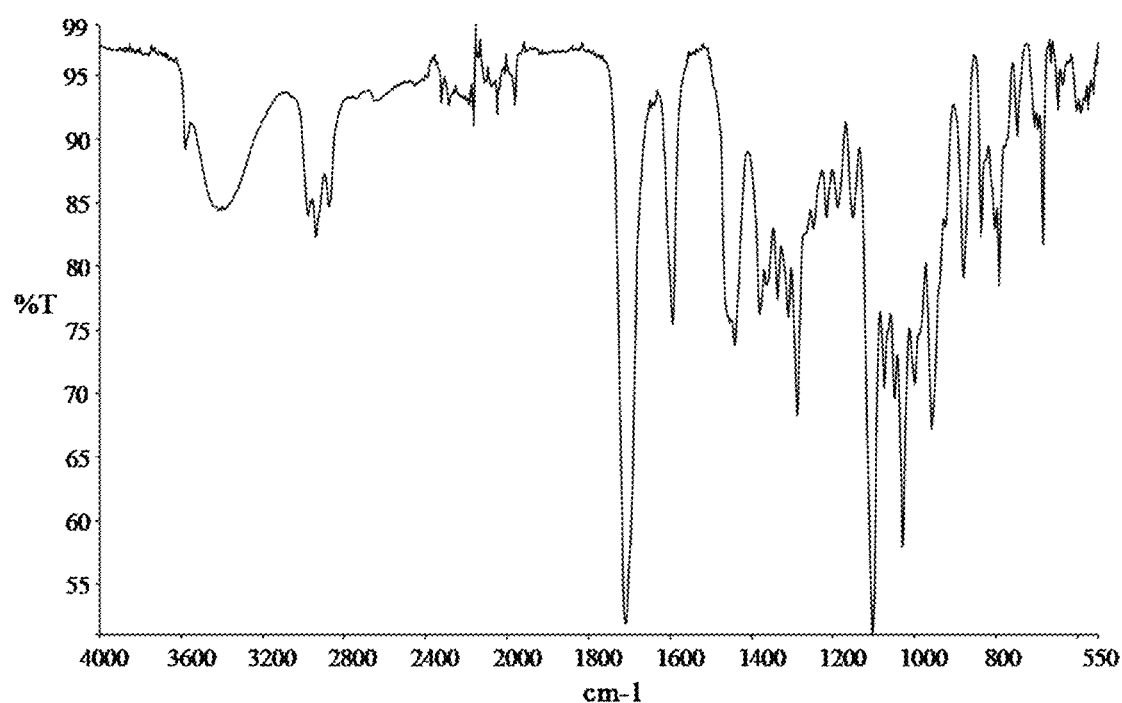
FIG. 5 FTIR of anhydrous ingenol 3-(3,5-diethylisoxazole-4-carboxylate)

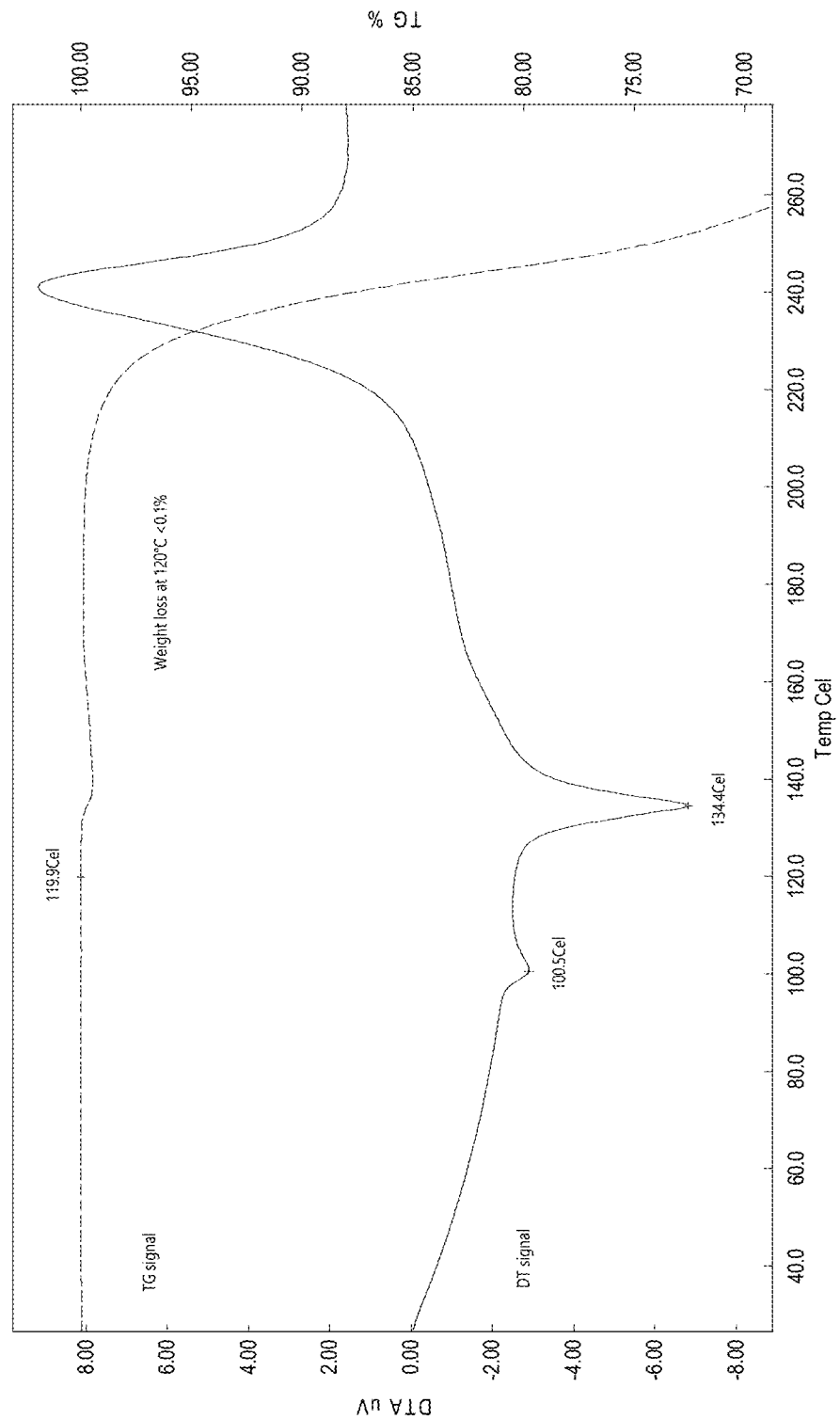
FIG. 6 TG/DTA of anhydrous ingenol 3-(3,5-diethylisoxazole-4-carboxylate)

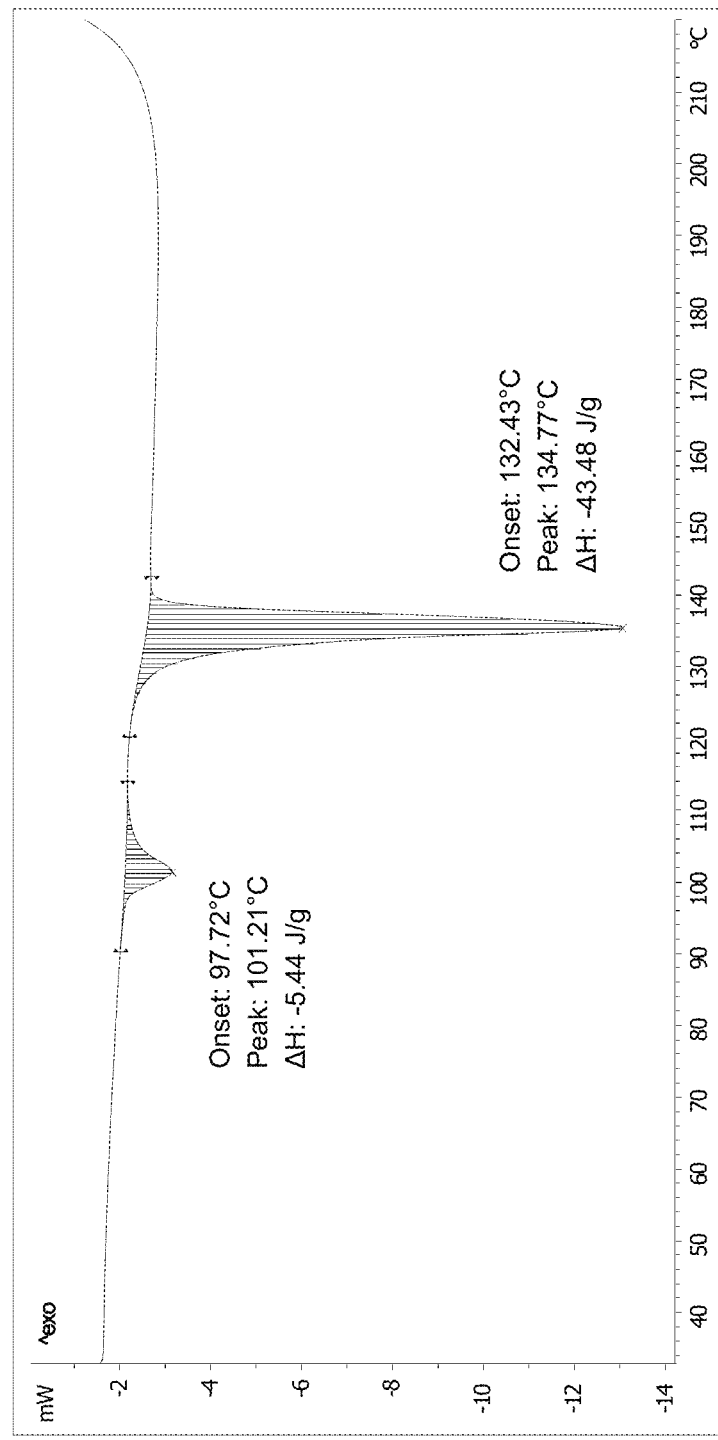
FIG. 7 DSC of anhydrous ingenol 3-(3,5-diethylisoxazole-4-carboxylate)

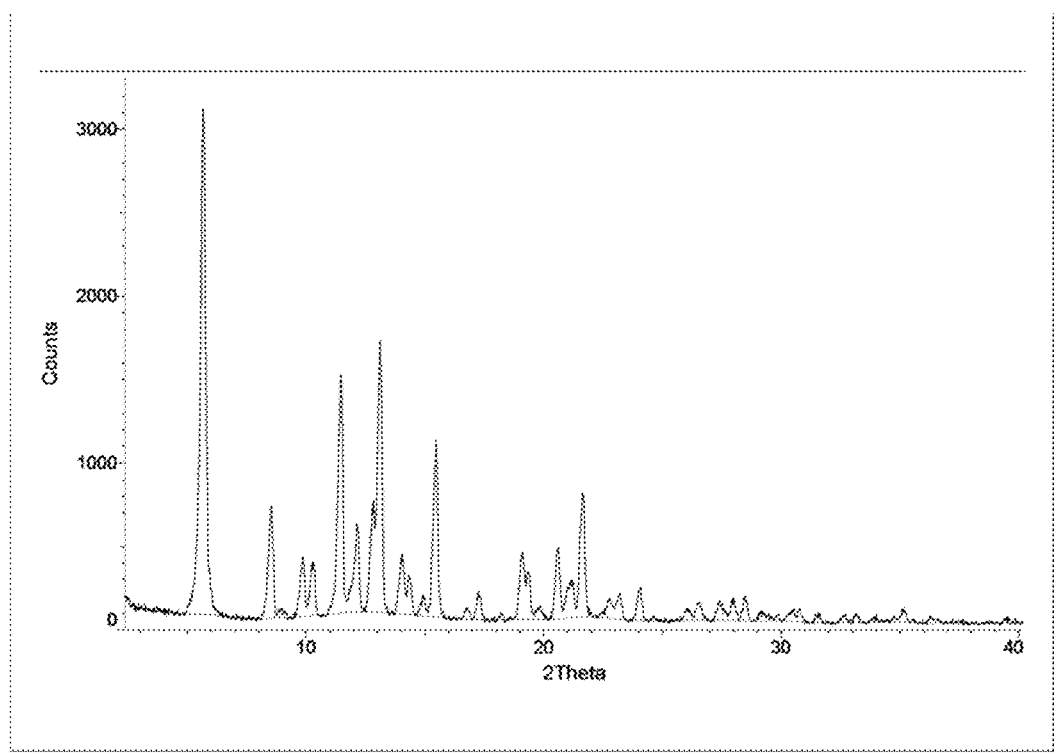
FIG. 8 XRPD of the acetone solvate of ingenol 3-(3,5-diethylisoxazole-4-carboxylate)

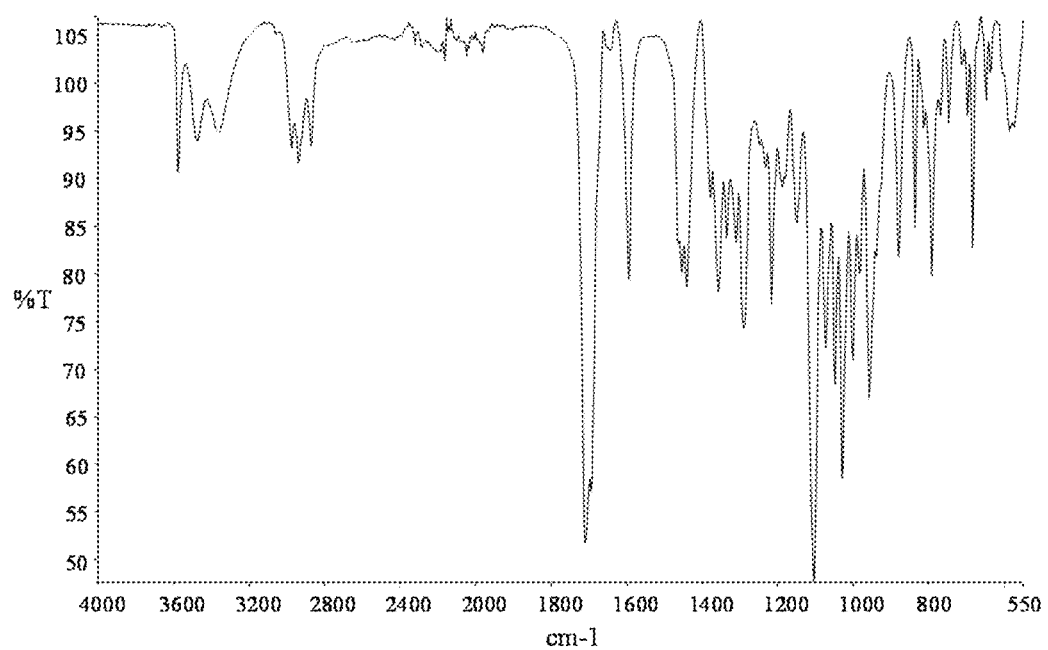
FIG. 9 FTIR of the acetone solvate of ingenol 3-(3,5-diethylisoxazole-4-carboxylate)

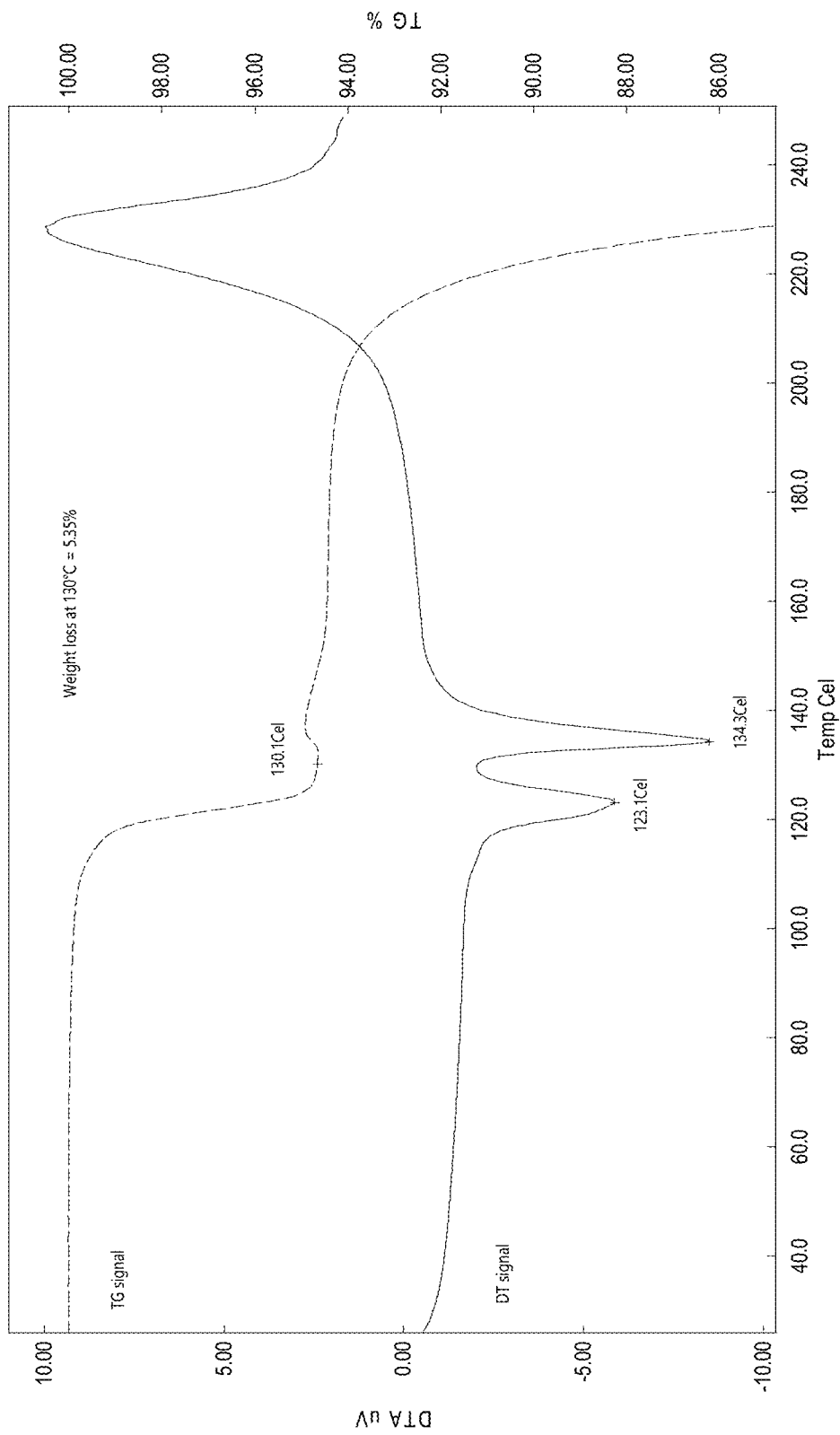
FIG. 10 TG/DTA of the acetone solvate of ingenol 3-(3,5-diethylisoxazole-4-carboxylate)

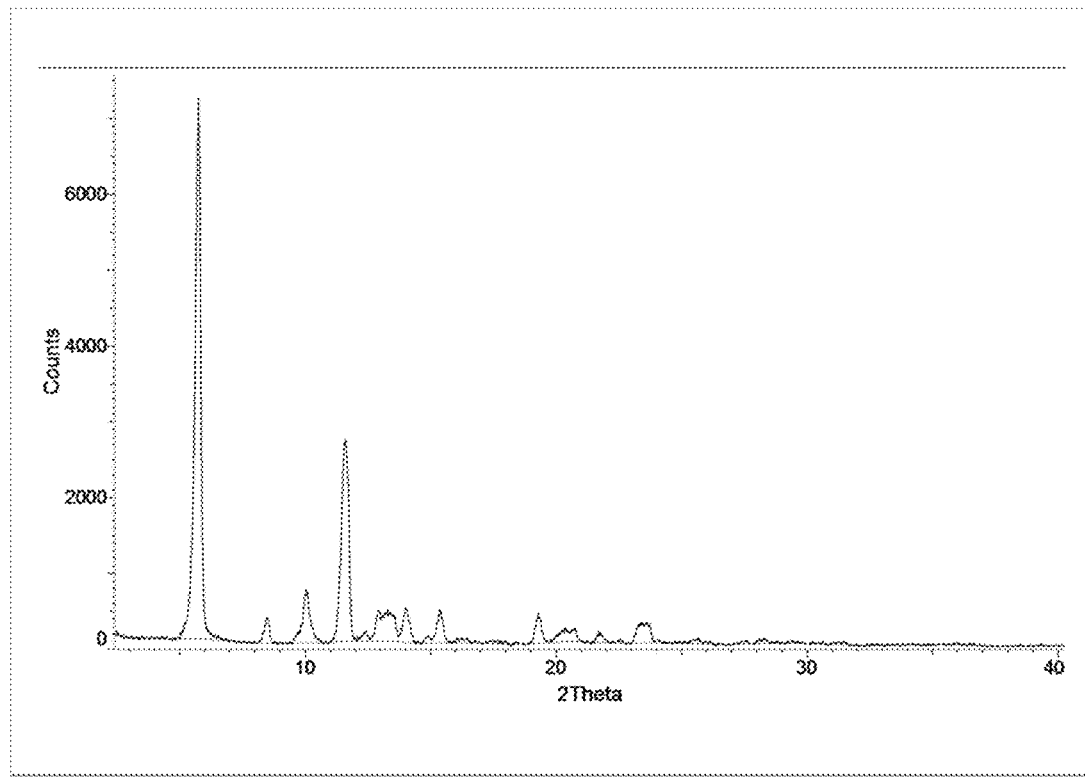
FIG. 11  XRPD of the dimethylcarbonate solvate of ingenol 3-(3,5-diethylisoxazole-4-carboxylate)

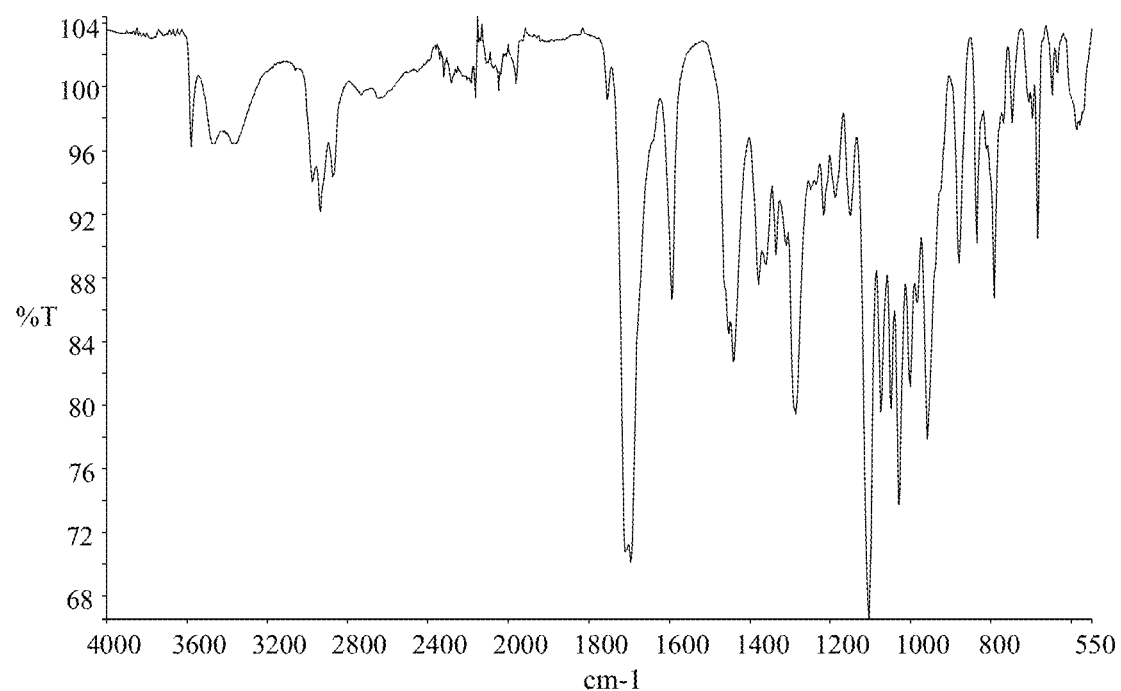
FIG. 12 FTIR of the dimethylcarbonate solvate of ingenol 3-(3,5-diethylisoxazole-4-carboxylate)

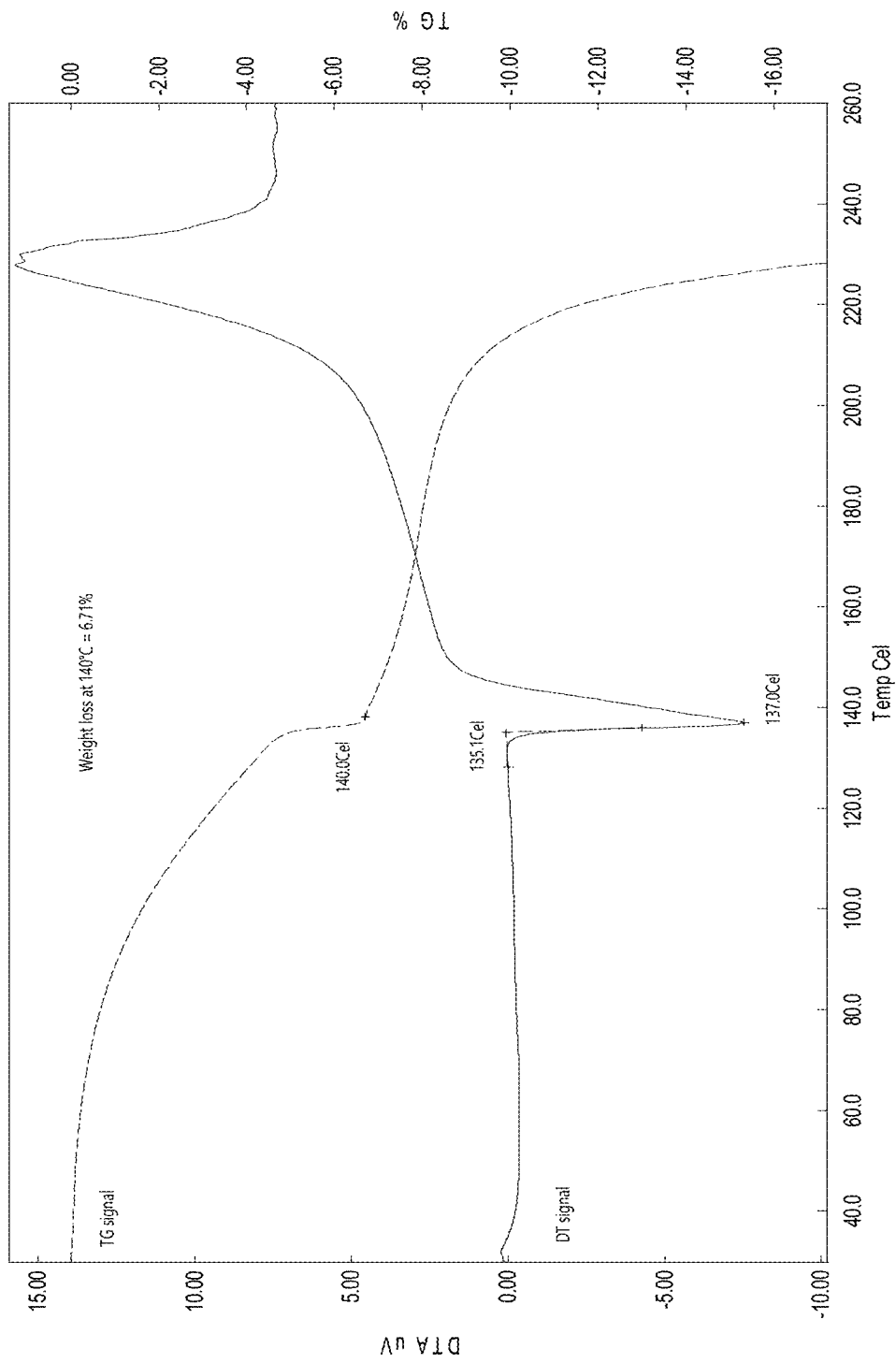
FIG. 13 TG/DTA of the dimethylcarbonate solvate of ingenol 3-(3,5-diethylisoxazole-4-carboxylate)

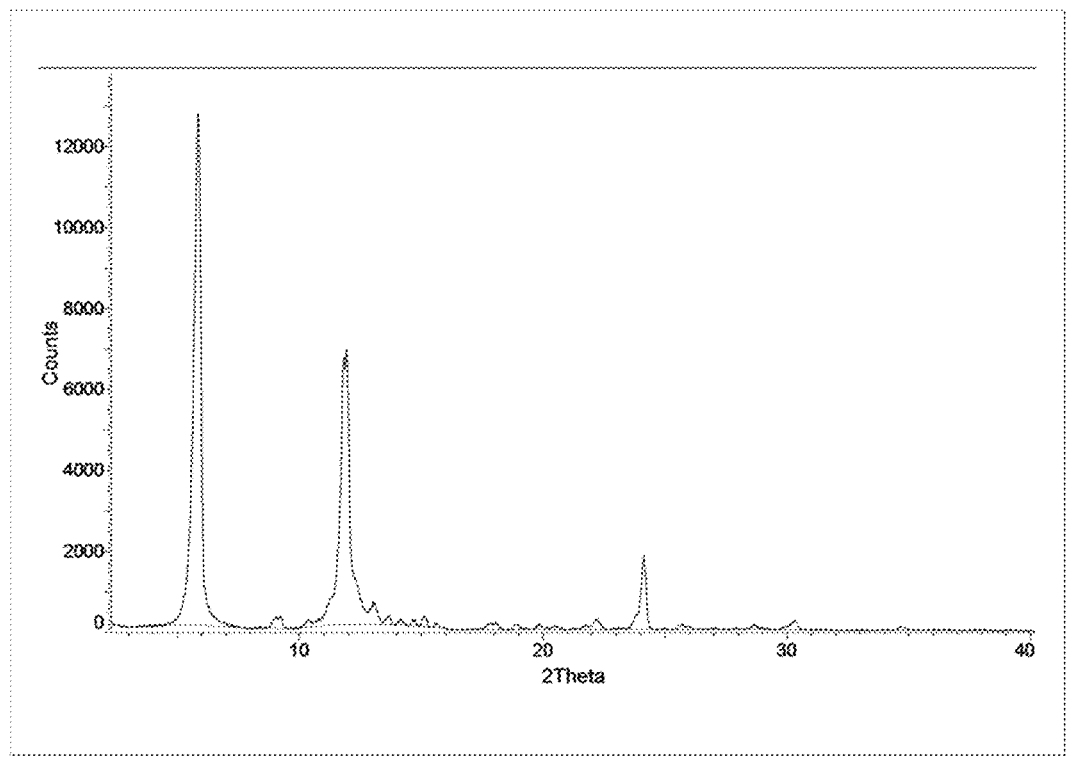
FIG. 14  XRPD of the isopropyl ether solvate of ingenol 3-(3,5-diethylisoxazole-4-carboxylate)

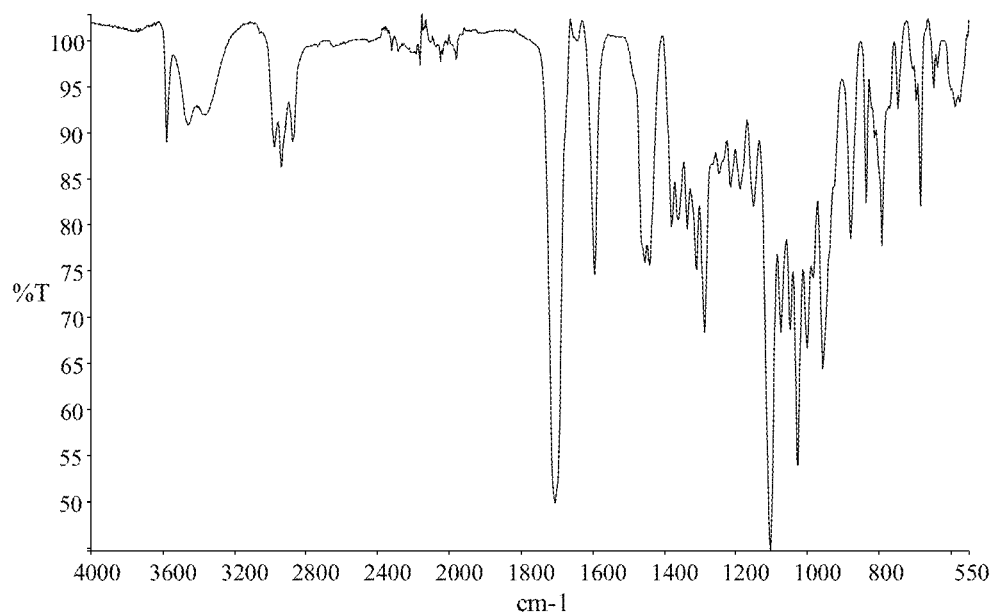
FIG. 15 FTIR of the isopropyl ether solvate of ingenol 3-(3,5-diethylisoxazole-4-carboxylate)

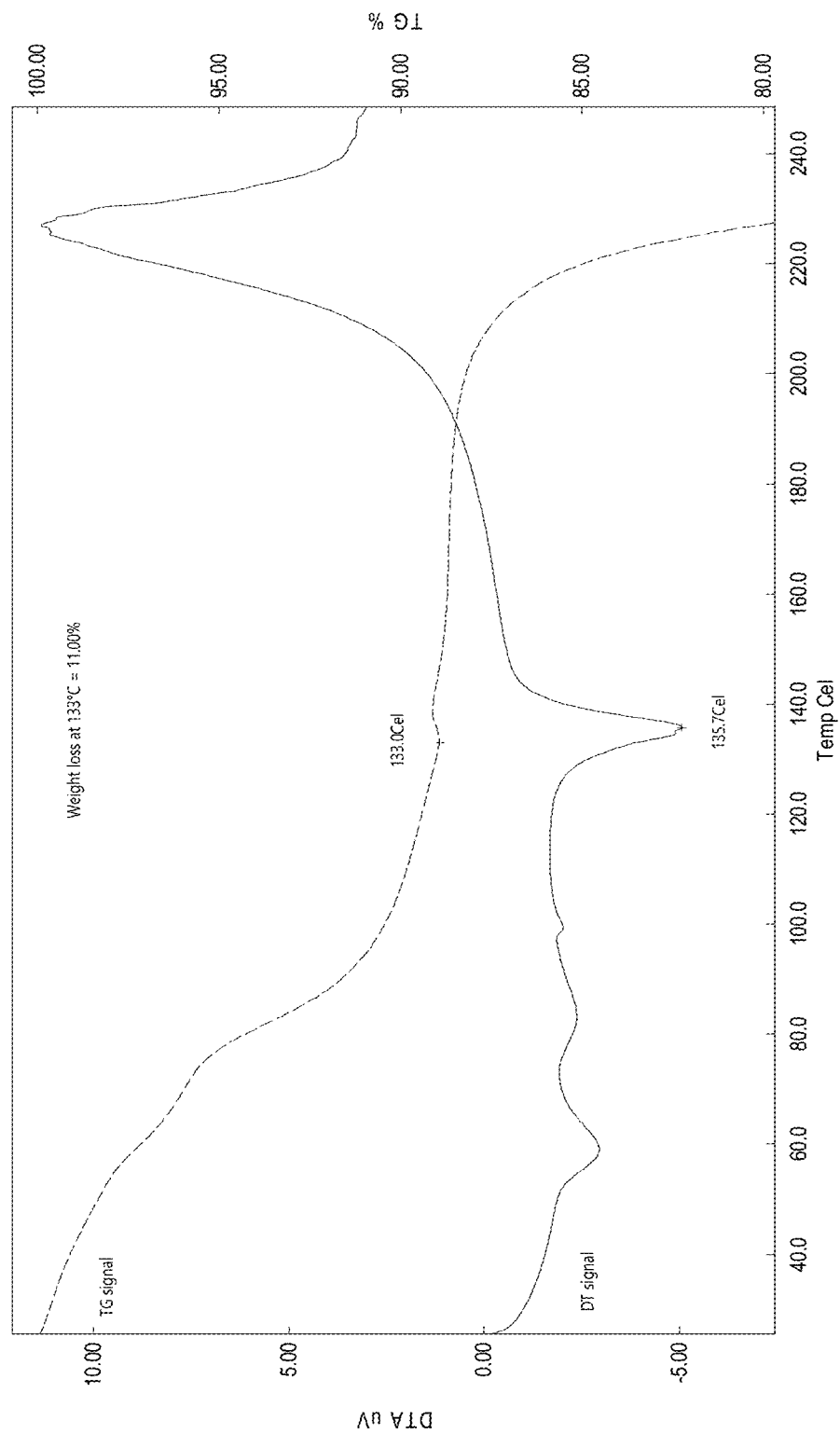
FIG. 16 TG/DTA of the isopropyl ether solvate of ingenol 3-(3,5-diethylisoxazole-4-carboxylate)

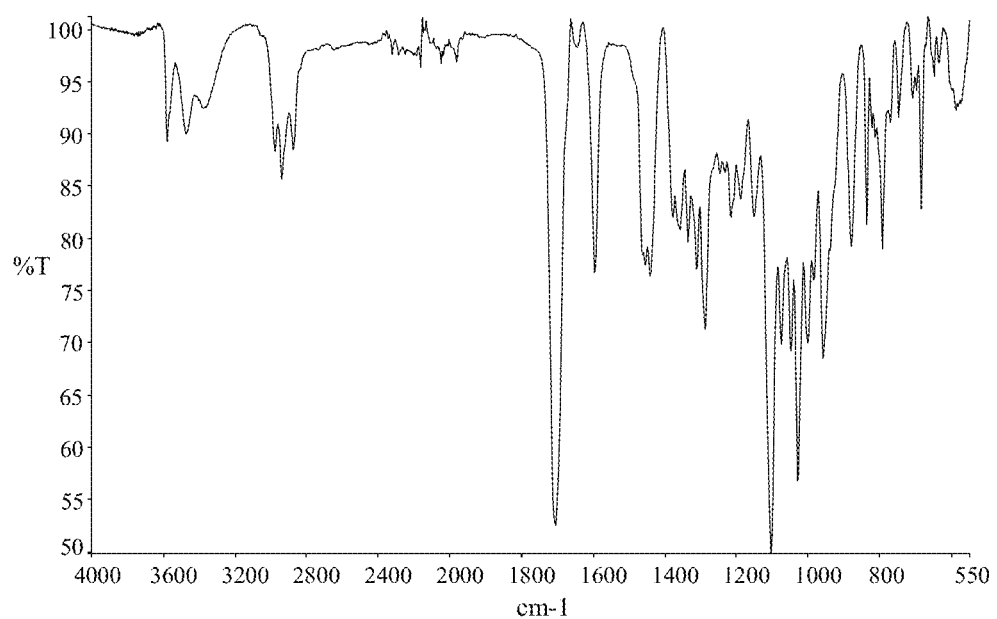
FIG. 17 FTIR of the acetonitrile solvate of ingenol 3-(3,5-diethylisoxazole-4-carboxylate)

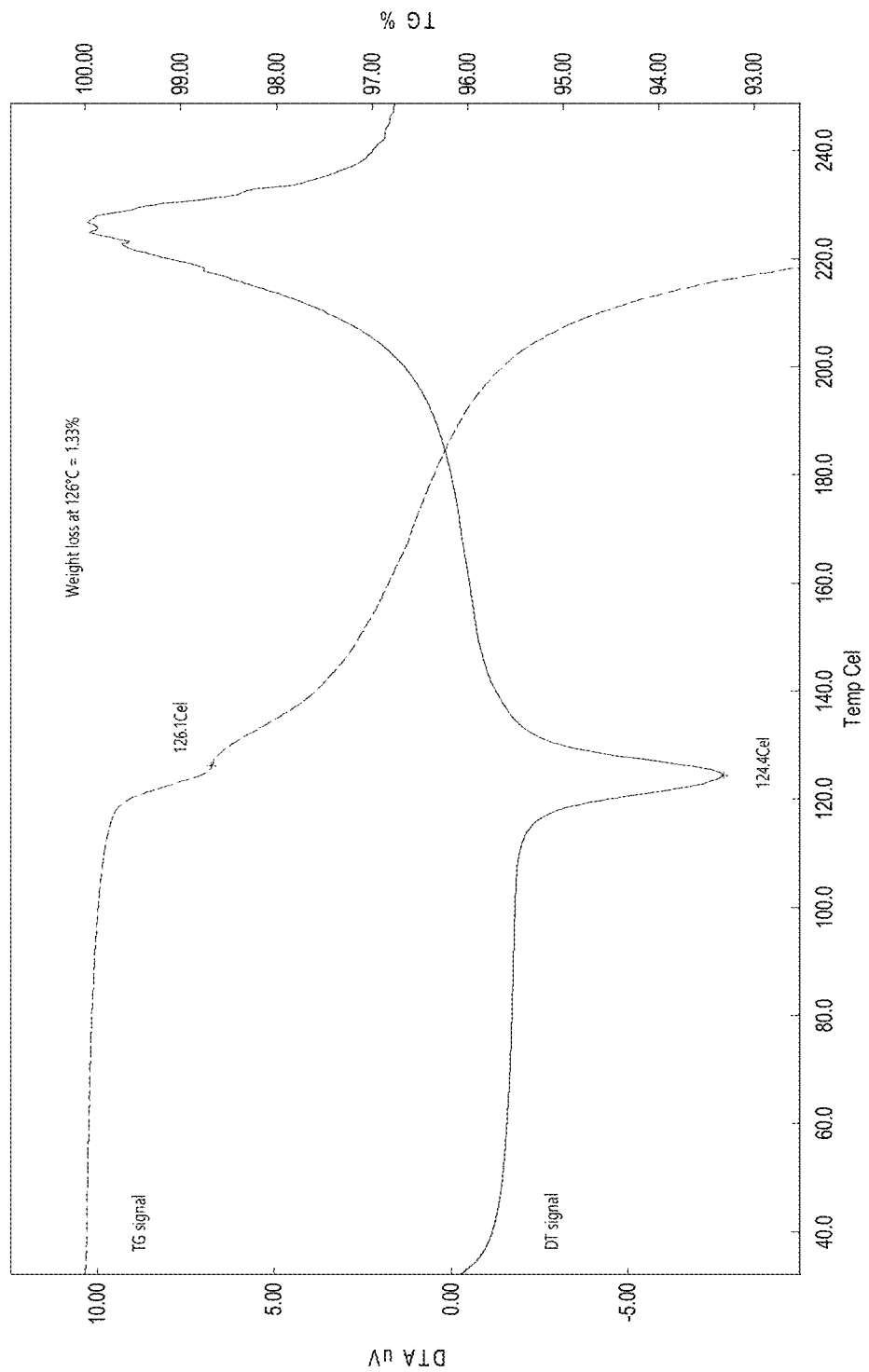
FIG. 18 TG/DTA of the acetonitrile solvate of ingenol 3-(3,5-diethylisoxazole-4-carboxylate)

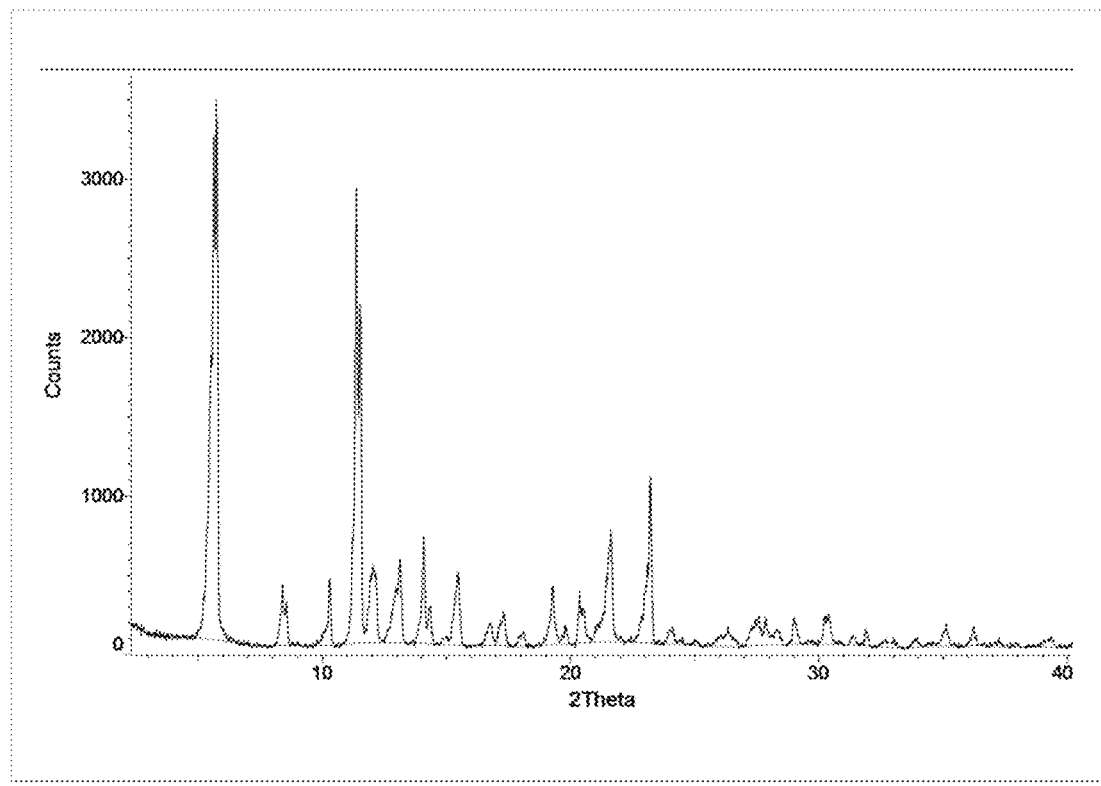
FIG. 19 XRPD of the toluene solvate of ingenol 3-(3,5-diethylisoxazole-4-carboxylate)

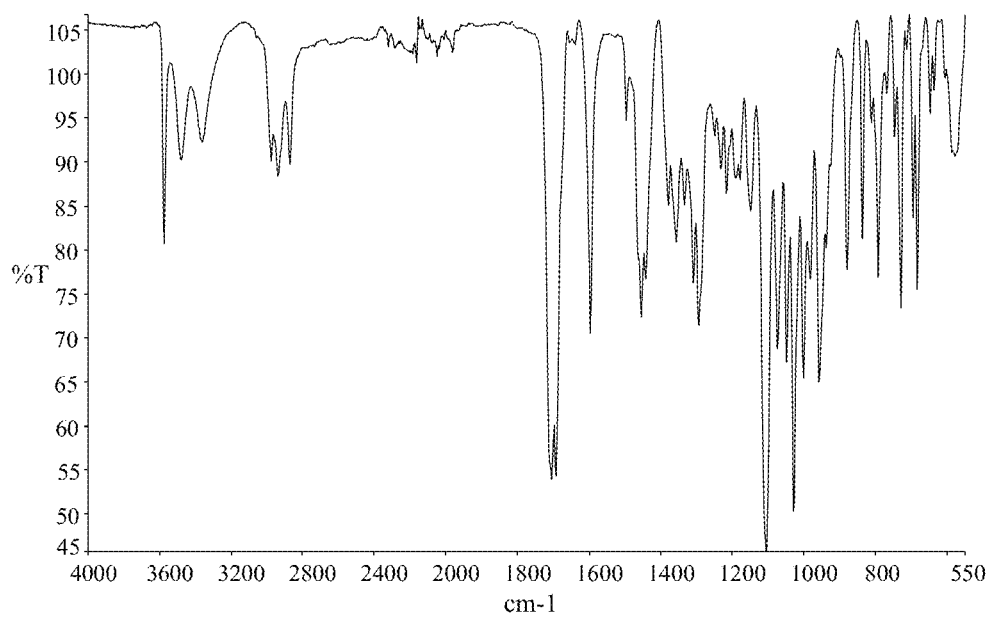
FIG. 20 FTIR of the toluene solvate of ingenol 3-(3,5-diethylisoxazole-4-carboxylate)

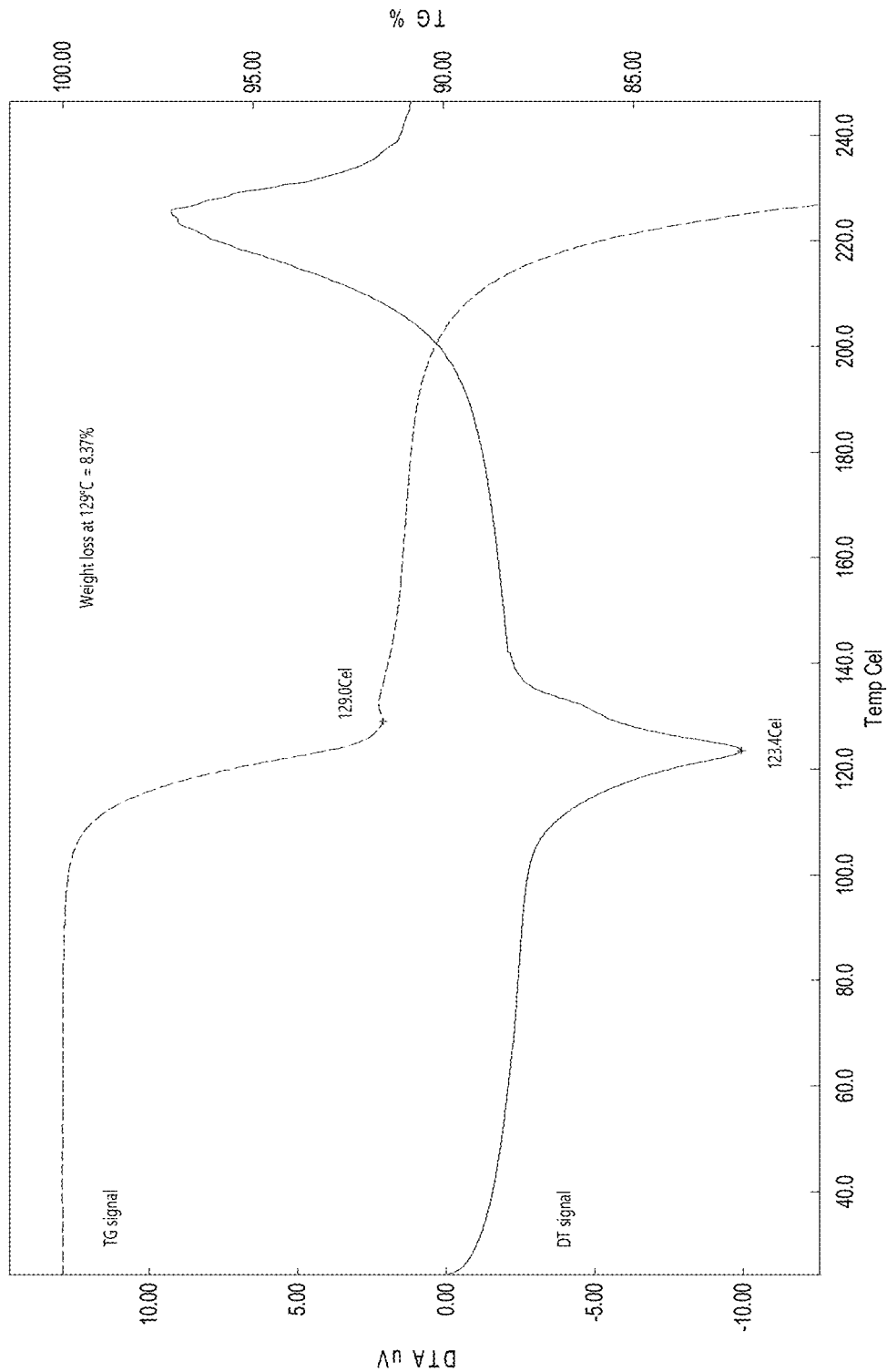
FIG. 21 TG/DTA of the toluene solvate of ingenol 3-(3,5-diethylisoxazole-4-carboxylate)

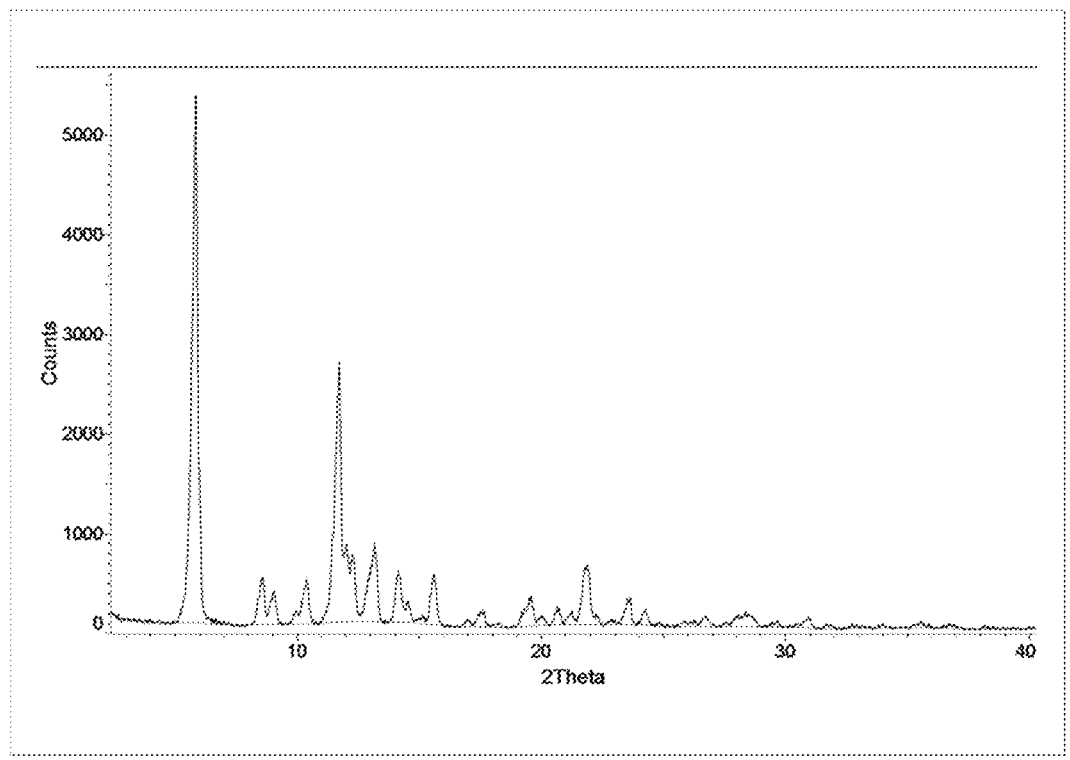
FIG. 22 XRPD of the nitromethane solvate of ingenol 3-(3,5-diethylisoxazole-4-carboxylate)

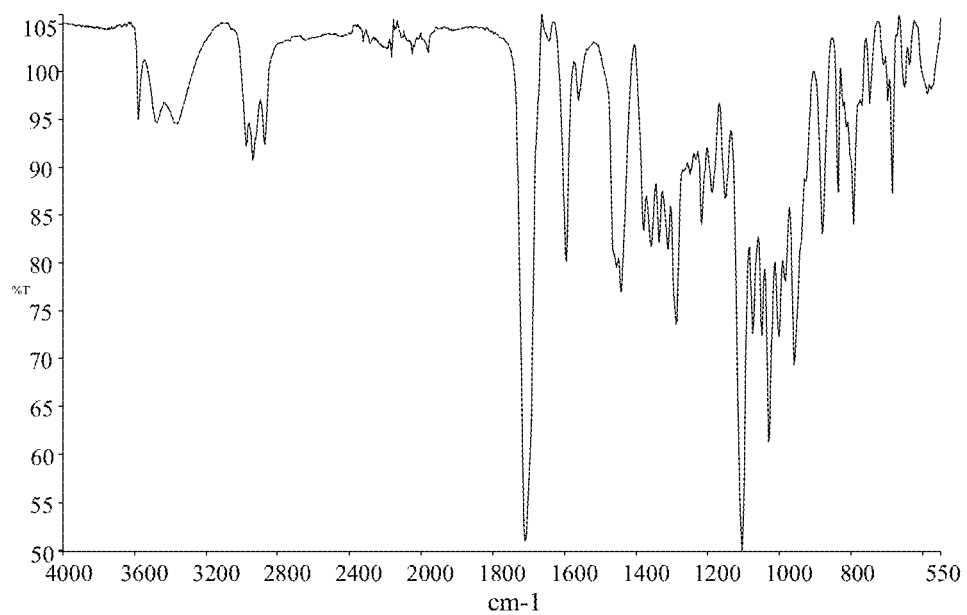
FIG. 23 FTIR of the nitromethane solvate of ingenol 3-(3,5-diethylisoxazole-4-carboxylate)

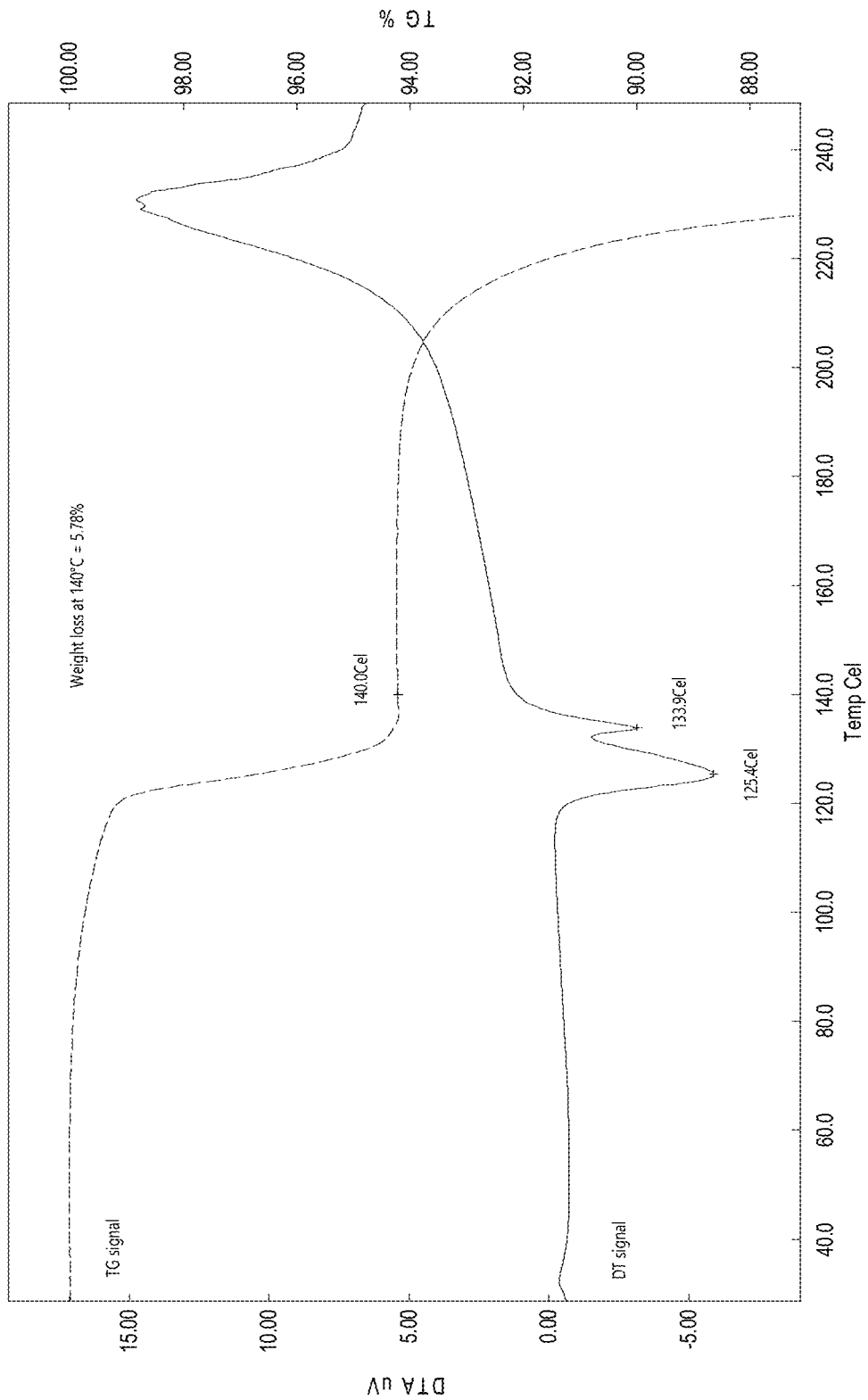
FIG. 24 TG/DTA of the nitromethane solvate of ingenol 3-(3,5-diethylisoxazole-4-carboxylate)

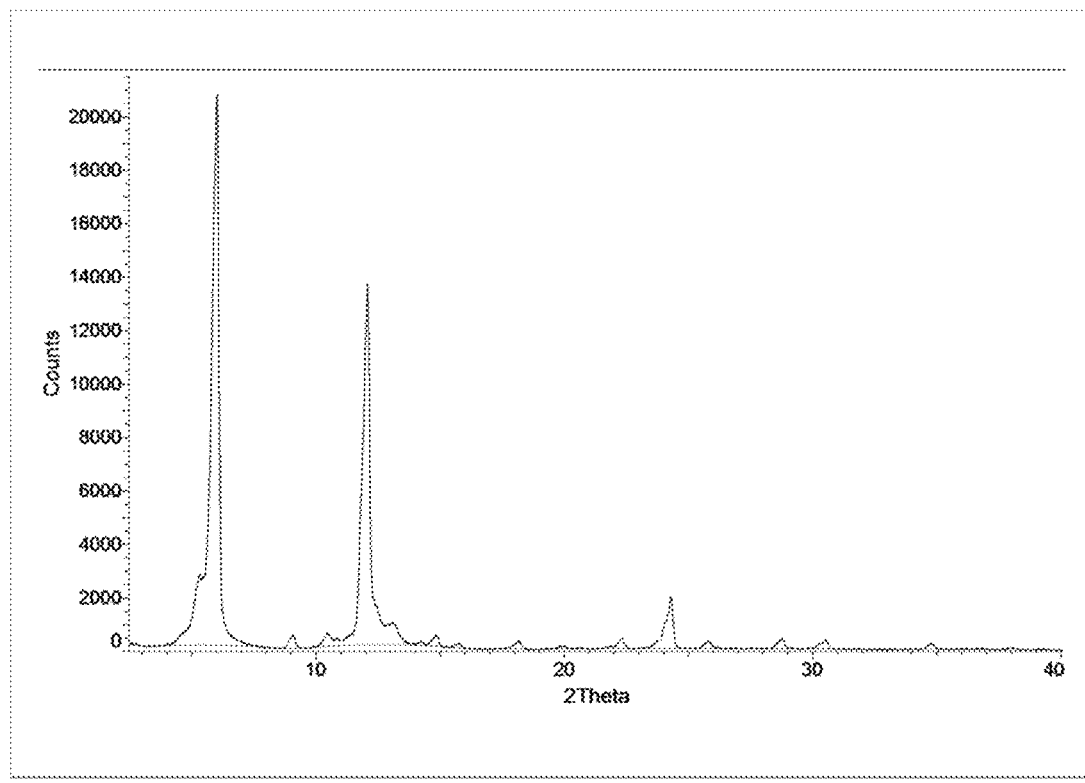
FIG. 25 XRPD of the mesitylene solvate of ingenol 3-(3,5-diethylisoxazole-4-carboxylate)

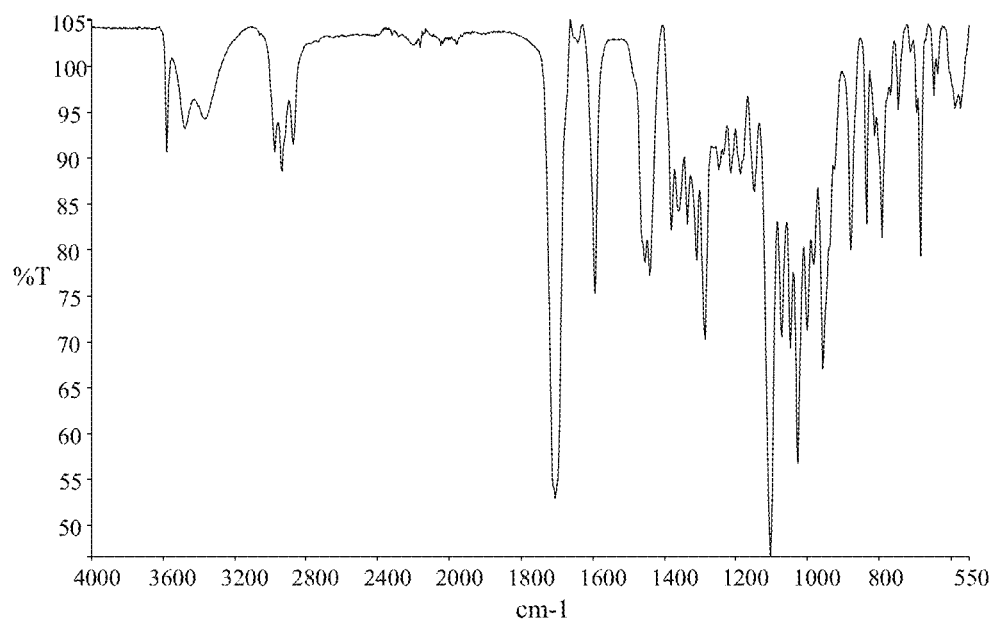
FIG. 26 FTIR of the mesitylene solvate of ingenol 3-(3,5-diethylisoxazole-4-carboxylate)

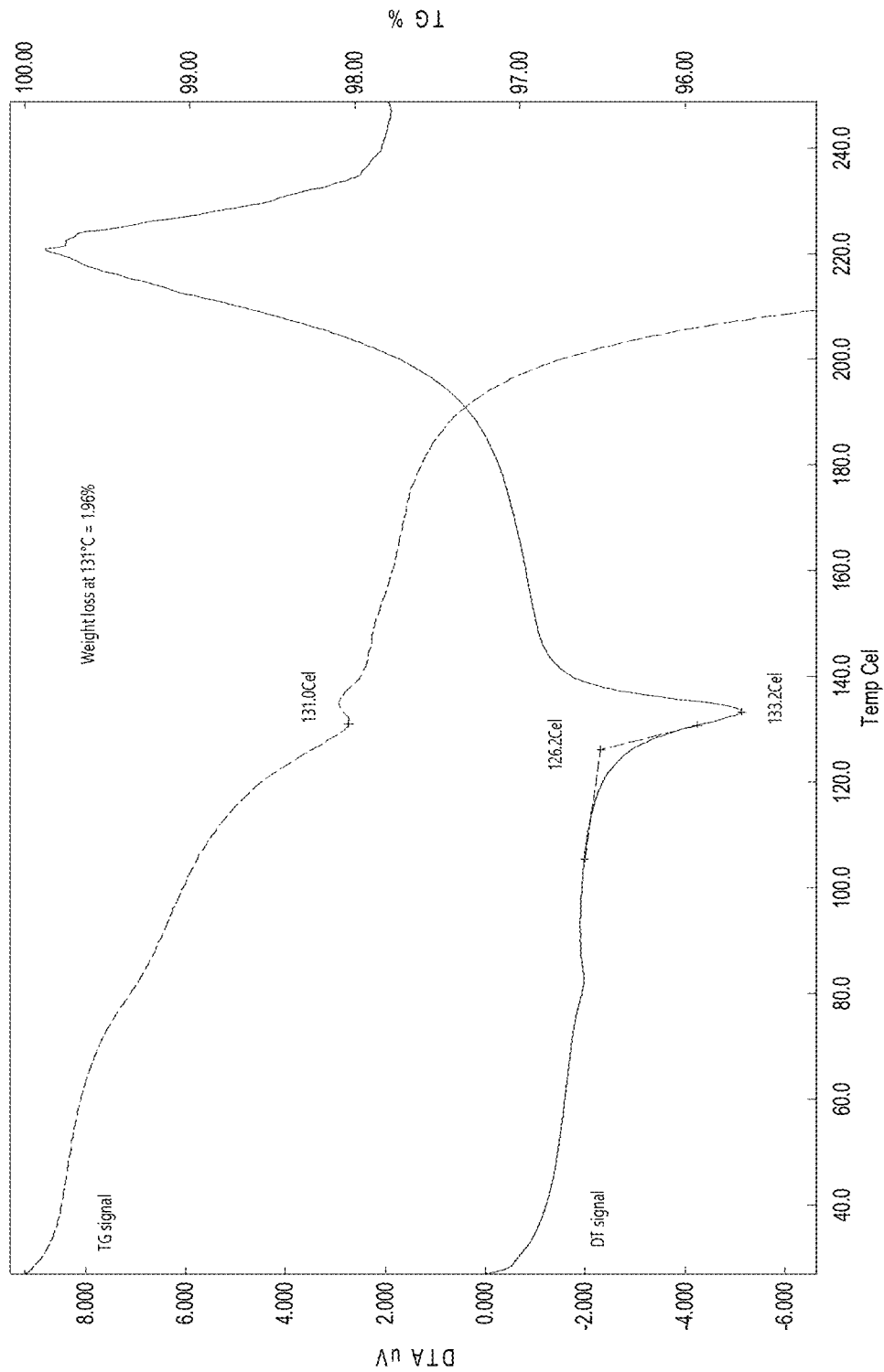
FIG. 27 TG/DTA of the mesitylene solvate of ingenol 3-(3,5-diethylisoxazole-4-carboxylate)

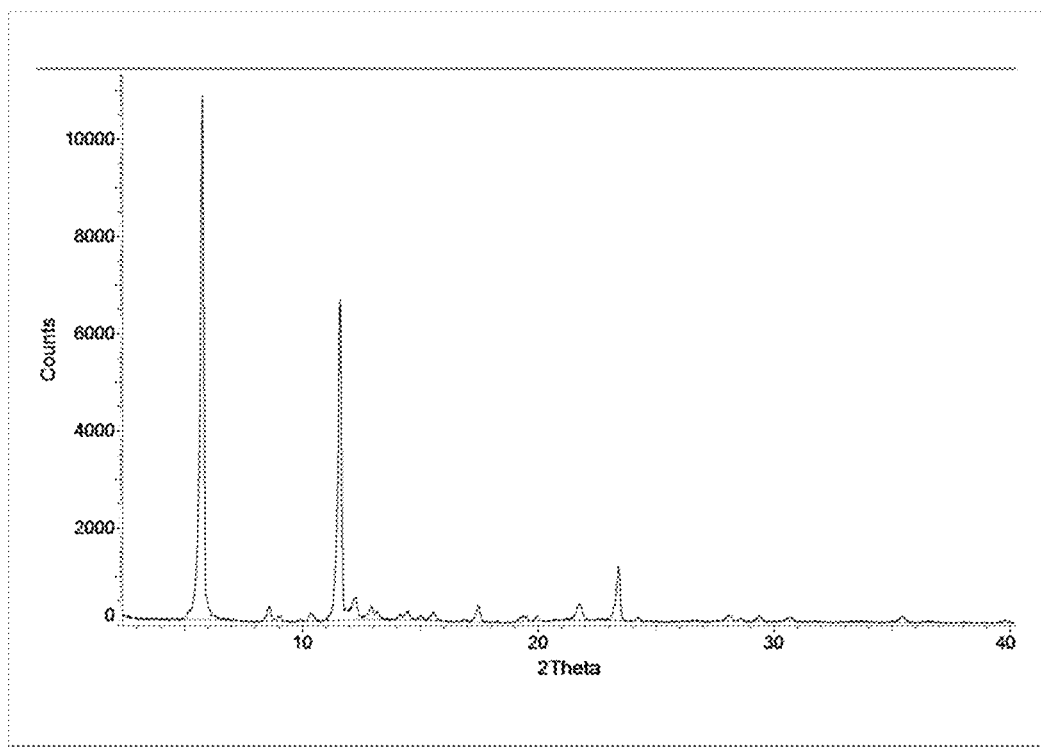
FIG. 28 XRPD of the dichloromethane/heptane solvate of ingenol 3-(3,5-diethylisoxazole-4-carboxylate)

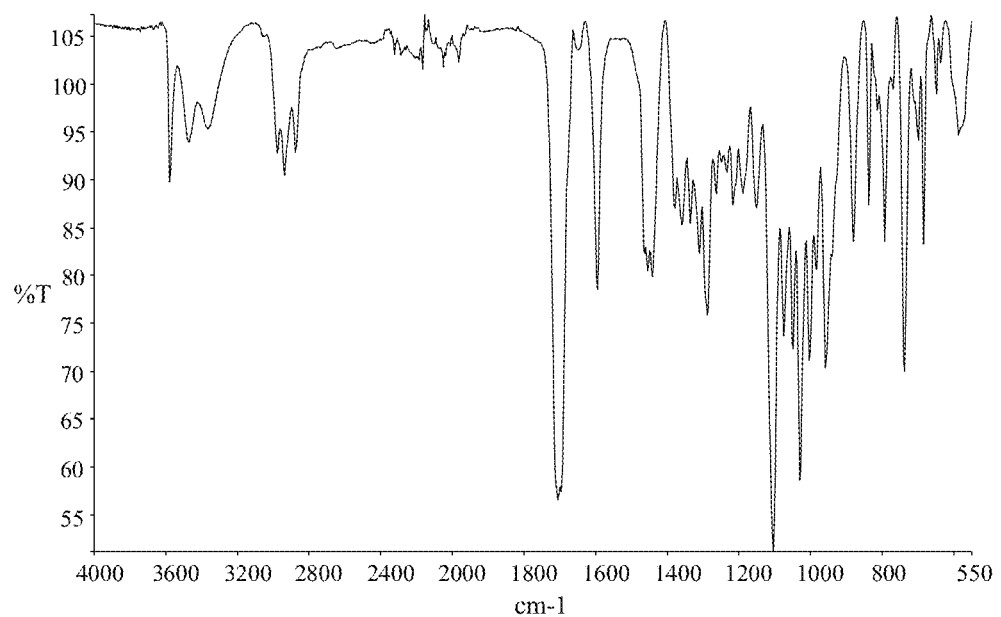
FIG. 29 FTIR of the dichloromethane/heptane solvate of ingenol 3-(3,5-diethylisoxazole-4-carboxylate)

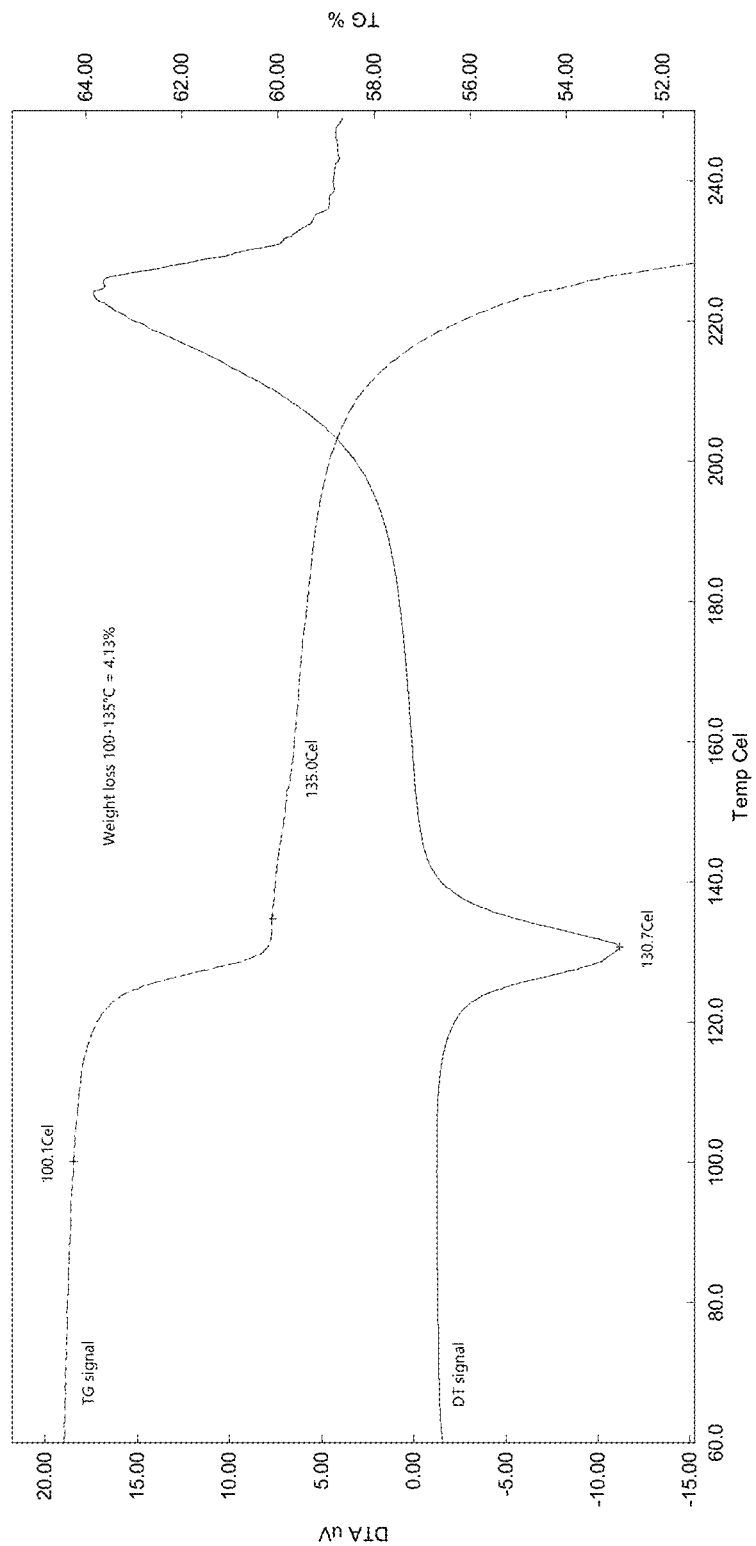
FIG. 30 TG/DTA of the dichloromethane/heptane solvate of ingenol 3-(3,5-diethylisoxazole-4-carboxylate)

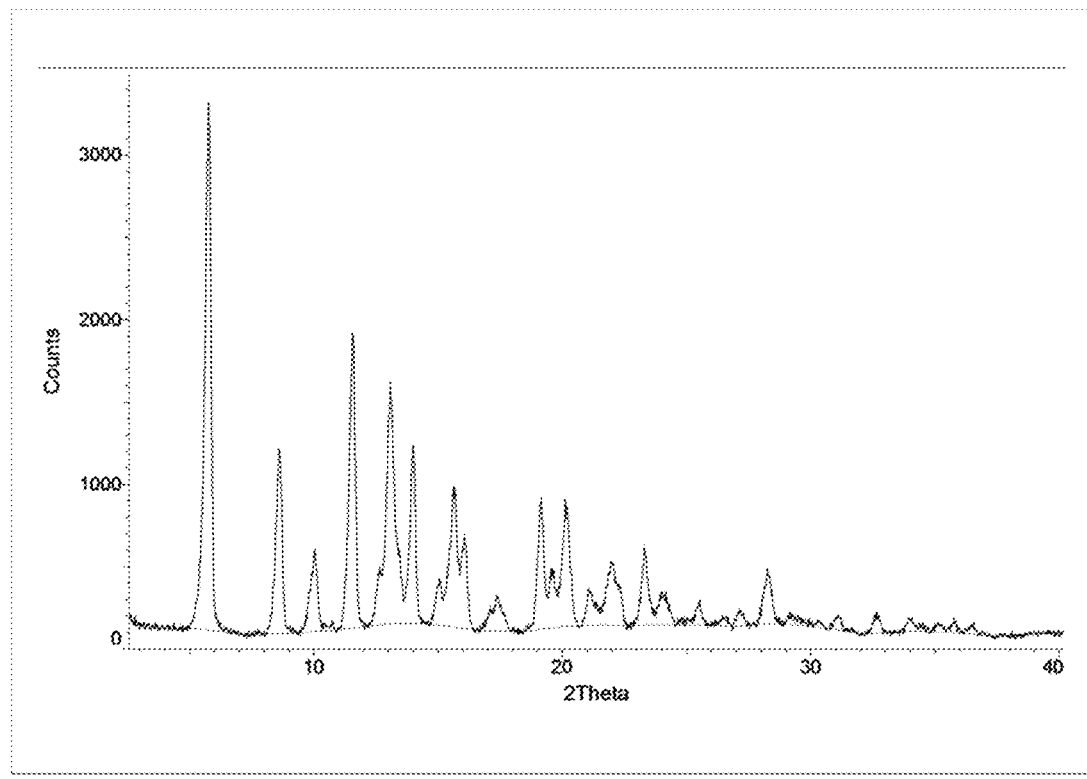
FIG. 31 XRPD of the ethyl acetate solvate of ingenol 3-(3,5-diethylisoxazole-4-carboxylate)

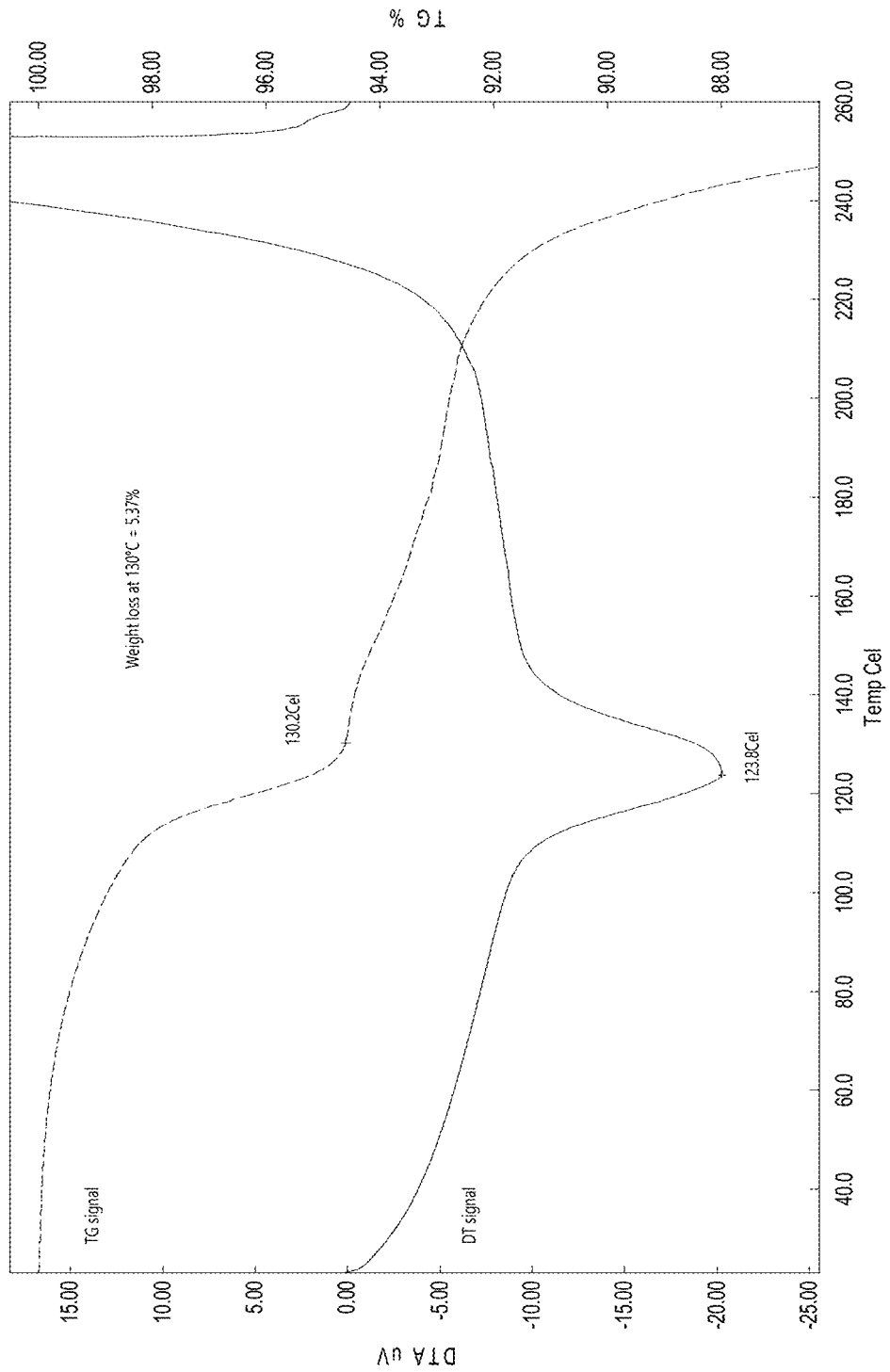
FIG. 32 TG/DTA of the ethyl acetate solvate of ingenol 3-(3,5-diethylisoxazole-4-carboxylate)

SOLID FORMS OF INGENOL 3-(3,5-DIETHYLISOXAZOLE-4-CARBOXYLATE) AND METHOD FOR PREPARING THE SAME

The present invention relates to solid forms of ingenol 3-(3,5-diethylisoxazole-4-carboxylate) and to methods for the preparation thereof.

BACKGROUND OF THE INVENTION

Ingenol-3-angelate is a diterpene ester that can be isolated from various *Euphorbia* species. The compound is currently used in the treatment of actinic keratosis. Angelic esters are prone to isomerization of the double bond to form the tiglate esters. Furthermore, ingenol-3-angelate is also prone to rearrangement to afford ingenol-5-angelate and ingenol-20-angelate.

WO2012/083953 discloses the synthesis of ingenol 3-(3,5-diethylisoxazole-4-carboxylate), a molecule devoid of the stability problems occurring to ingenol 3-angelate. The molecule is presently subject of clinical development for the treatment of actinic keratosis. The characteristics of the solid form of ingenol 3-(3,5-diethylisoxazole-4-carboxylate) have not been reported. The discovery of new forms of pharmaceutically useful compounds provides an opportunity to improve their performance.

BRIEF SUMMARY OF THE INVENTION

In one embodiment, the invention relates to the amorphous form of ingenol 3-(3,5-diethylisoxazole-4-carboxylate), characterized by an XRPD pattern with absence of diffraction peaks and a FTIR pattern with peaks at about 2940-1708-1597-1444-1380-1288-1188-1105-1033-959-880-803-678±4 $cm^{-1}$.

Another embodiment of the invention encompasses a crystalline anhydrous form of ingenol 3-(3,5-diethylisoxazole-4-carboxylate) (Form A) characterized by a XRPD pattern with peaks at about 6.0-9.4-11.9-13.2-13.8-15.3-19.1-20.1-24.0-28.1±0.2 degrees two theta and a FTIR pattern with peaks at about 3582-3416-2979-2940-1709-1594-1442-1380-1288-1103-1030-959-881-794-686±4 $cm^{-1}$.

Another embodiment of the invention encompasses solid solvates of ingenol 3-(3,5-diethylisoxazole-4-carboxylate) useful as intermediates for the preparation the amorphous and of the crystalline anhydrous form of the invention.

Said solvates include:

an acetone solvate of ingenol 3-(3,5-diethylisoxazole-4-carboxylate) characterized by a XRPD pattern with peaks at about 5.7-8.5-11.4-12.1-13.1-15.4-19.1-20.6-21.6-24.0±0.2 degrees two theta and a FTIR spectrum with peaks at about 3579-3478-3364-2940-1711-1695-1595-1442-1358-1217-1105-1033-959-880-793-684±4 $cm^{-1}$;

a dimethylcarbonate solvate of ingenol 3-(3,5-diethylisoxazole-4-carboxylate) characterized by a XRPD pattern with peaks at about 5.7-8.4-10.1-11.6-13.0-14.0-15.4-19.3-21.7-23.4±0.2 degrees two theta and a FTIR spectrum with peaks at about 3581-3473-2939-1754-1709-1696-1594-1441-1287-1151-1105-1030-959-880-794-685±4 $cm^{-1}$;

an isopropyl ether solvate of ingenol 3-(3,5-diethylisoxazole-4-carboxylate) characterized by a XRPD pattern with peaks at about 5.9-9.2-10.4-11.8-11.9-13.1-13.6-15.1-17.9-22.2-24.1-30.3±0.2 degrees two theta and a FTIR spectrum with peaks at about 3581-3463-2940-1705-1644-1595-1456-1442-1288-1152-1105-1029-959-881-837-794-686±4 $cm^{-1}$;

an acetonitrile solvate of ingenol 3-(3,5-diethylisoxazole-4-carboxylate) characterized by FTIR spectrum with peaks at about 3581-3474-3378-2940-1706-1644-1596-1456-1312-1288-1152-1104-1076-1049-1030-959-880-794-685±4 $cm^{-1}$;

a toluene solvate of ingenol 3-(3,5-diethylisoxazole-4-carboxylate) characterized by a XRPD pattern with peaks at about 5.6-5.7-8.4-8.5-10.3-11.4-11.5-12.1-13.1-14.1-15.4-19.3-21.6-23.2±0.2 degrees two theta and a FTIR spectrum with peaks at about 3576-3481-2874-1706-1693-1640-1597-1497-1455-1309-1295-1106-1074-1049-1003-958-880-837-794-730-696-684-649±4 $cm^{-1}$.

a nitromethane solvate of ingenol 3-(3,5-diethylisoxazole-4-carboxylate) characterized by a XRPD pattern with peaks at about 5.8-8.6-9.0-10.4-11.7-13.2-14.1-15.6-21.9-23.6-24.2±0.2 degrees two theta and a FTIR spectrum with peaks at about 3579-3476-2876-1710-1643-1596-1560-1442-1358-1336-1288-1218-1105-1030-959-880-837 794-685±4 $cm^{-1}$;

a mesitylene solvate of ingenol 3-(3,5-diethylisoxazole-4-carboxylate) characterized by a XRPD pattern with peaks at about 5.3-6.0-9.1-10.5-12.1-13.0-14.8-18.2-22.3-24.3-25.8-28.6-30.6-34.7±0.2 degrees two theta and a FTIR pattern with peaks at about 3580-3479-2876-1705-1642-1595-1560-1455-1441-1381-1311-1288-1150-1105-1074-1029-1003-958-880-836-794-685±4 $cm^{-1}$;

a dichloromethane/heptane solvate of ingenol 3-(3,5-diethylisoxazole-4-carboxylate) characterized by a XRPD pattern with peaks at about 5.7-8.6-9.0-10.4-11.6-12.2-12.9-14.4-15.5-17.5-19.9-21.7-22.4-28.1-29.4±0.2 degrees two theta and a FTIR pattern with peaks at about 3578-3474-2876-1705-1652-1596-1454-1442-1288-1217-1152-1105-1075-1050-1030-1003-958-880-837-794-770-739-700-685±4 $cm^{-1}$;

an ethyl acetate solvate of ingenol 3-(3,5-diethylisoxazole-4-carboxylate) characterized by a XRPD pattern with peaks at about 5.8-8.6-10.0-11.6-12.7-13.1-14.0-15.6-16.0-19.1-20.2-22.0-23.2±0.2 degrees two theta.

BRIEF DESCRIPTION OF THE FIGURES

FIG. 1 depicts the X-Ray Powder Diffraction (XRPD) analysis of the amorphous form of ingenol 3-(3,5-diethylisoxazole-4-carboxylate).

FIG. 2 depicts the Fourier Transform InfraRed (FTIR) analysis of the amorphous form of ingenol 3-(3,5-diethylisoxazole-4-carboxylate).

FIG. 3 depicts Differential Thermal Analysis (DTA) and ThermoGravimetric analysis (TG) of the amorphous form of ingenol 3-(3,5-diethylisoxazole-4-carboxylate).

FIG. 4 depicts the X-Ray Powder Diffraction (XRPD) analysis of the anhydrous (Form A) ingenol 3-(3,5-diethylisoxazole-4-carboxylate).

FIG. 5 depicts the Fourier Transform InfraRed (FTIR) analysis of anhydrous (Form A) ingenol 3-(3,5-diethylisoxazole-4-carboxylate).

FIG. 6 depicts Differential Thermal Analysis (DTA) and ThermoGravimetric analysis (TG) of anhydrous (Form A) ingenol 3-(3,5-diethylisoxazole-4-carboxylate).

FIG. 7 depicts Differential Scanning Calorimetry (DSC) analysis of anhydrous (Form A) ingenol 3-(3,5-diethylisoxazole-4-carboxylate).

FIG. 8 depicts the X-Ray Powder Diffraction (XRPD) analysis of the acetone solvate of ingenol 3-(3,5-diethylisoxazole-4-carboxylate).

FIG. 9 depicts the Fourier Transform InfraRed (FTIR) analysis of the acetone solvate of ingenol 3-(3,5-diethylisoxazole-4-carboxylate).

FIG. 10 depicts Differential Thermal Analysis (DTA) and ThermoGravimetric analysis (TG) of the acetone solvate of ingenol 3-(3,5-diethylisoxazole-4-carboxylate).

FIG. 11 depicts the X-Ray Powder Diffraction (XRPD) analysis of the dimethylcarbonate solvate of ingenol 3-(3,5-diethylisoxazole-4-carboxylate).

FIG. 12 depicts a Fourier Transform InfraRed (FTIR) analysis of the dimethylcarbonate solvate of ingenol 3-(3,5-diethylisoxazole-4-carboxylate).

FIG. 13 depicts Differential Thermal Analysis (DTA) and ThermoGravimetric analysis (TG) of the dimethylcarbonate solvate of ingenol 3-(3,5-diethylisoxazole-4-carboxylate).

FIG. 14 depicts the X-Ray Powder Diffraction (XRPD) analysis of the Isopropyl ether solvate of ingenol 3-(3,5-diethylisoxazole-4-carboxylate).

FIG. 15 depicts the Fourier Transform InfraRed (FTIR) analysis of the Isopropyl ether solvate of ingenol 3-(3,5-diethylisoxazole-4-carboxylate).

FIG. 16 depicts Differential Thermal Analysis (DTA) and ThermoGravimetric analysis (TG) of the Isopropyl ether solvate of ingenol 3-(3,5-diethylisoxazole-4-carboxylate).

FIG. 17 depicts the Fourier Transform InfraRed (FTIR) analysis of the acetonitrile solvate of ingenol 3-(3,5-diethylisoxazole-4-carboxylate).

FIG. 18 depicts Differential Thermal Analysis (DTA) and ThermoGravimetric analysis (TG) of the acetonitrile solvate of ingenol 3-(3,5-diethylisoxazole-4-carboxylate).

FIG. 19 depicts the X-Ray Powder Diffraction (XRPD) analysis of the toluene solvate of ingenol 3-(3,5-diethylisoxazole-4-carboxylate).

FIG. 20 depicts a Fourier Transform InfraRed (FTIR) analysis of the toluene solvate of ingenol 3-(3,5-diethylisoxazole-4-carboxylate).

FIG. 21 depicts Differential Thermal Analysis (DTA) and ThermoGravimetric analysis (TG) of the toluene solvate of ingenol 3-(3,5-diethylisoxazole-4-carboxylate).

FIG. 22 depicts the X-Ray Powder Diffraction (XRPD) analysis of the nitromethane solvate of ingenol 3-(3,5-diethylisoxazole-4-carboxylate).

FIG. 23 depicts the Fourier Transform InfraRed (FTIR) analysis of the nitromethane solvate of ingenol 3-(3,5-diethylisoxazole-4-carboxylate).

FIG. 24 depicts Differential Thermal Analysis (DTA) and ThermoGravimetric analysis (TG) of the nitromethane solvate of ingenol 3-(3,5-diethylisoxazole-4-carboxylate).

FIG. 25 depicts the X-Ray Powder Diffraction (XRPD) analysis of the mesitylene solvate of ingenol 3-(3,5-diethylisoxazole-4-carboxylate).

FIG. 26 depicts the Fourier Transform InfraRed (FTIR) analysis of the mesitylene solvate of ingenol 3-(3,5-diethylisoxazole-4-carboxylate).

FIG. 27 depicts Differential Thermal Analysis (DTA) and ThermoGravimetric analysis (TG) of the mesitylene solvate of ingenol 3-(3,5-diethylisoxazole-4-carboxylate).

FIG. 28 depicts the X-Ray Powder Diffraction (XRPD) analysis of the dichloromethane/heptane solvate of ingenol 3-(3,5-diethylisoxazole-4-carboxylate).

FIG. 29 depicts a Fourier Transform InfraRed (FTIR) analysis of the dichloromethane/heptane solvate of ingenol 3-(3,5-diethylisoxazole-4-carboxylate).

FIG. 30 depicts Differential Thermal Analysis (DTA) and ThermoGravimetric analysis (TG) of the dichloromethane/heptane solvate of ingenol 3-(3,5-diethylisoxazole-4-carboxylate).

FIG. 31 depicts the X-Ray Powder Diffraction (XRPD) analysis of the ethyl acetate solvate of ingenol 3-(3,5-diethylisoxazole-4-carboxylate).

FIG. 32 depicts Differential Thermal Analysis (DTA) and ThermoGravimetric analysis (TG) of the ethyl acetate solvate of ingenol 3-(3,5-diethylisoxazole-4-carboxylate).

DETAILED DESCRIPTION OF THE INVENTION

The invention provides amorphous and crystalline anhydrous solid forms of ingenol 3-(3,5-diethylisoxazole-4-carboxylate) and methods of preparing thereof. The solid forms of the invention provide opportunities to improve the pharmaceutical performance characteristics of ingenol 3-(3,5-diethylisoxazole-4-carboxylate).

The invention also provides solvates of ingenol 3-(3,5-diethylisoxazole-4-carboxylate) useful for the preparation and/or the purification of the amorphous and crystalline anhydrous solid forms of ingenol 3-(3,5-diethylisoxazole-4-carboxylate), In one embodiment, the invention encompasses the amorphous form of ingenol 3-(3,5-diethylisoxazole-4-carboxylate), characterized by a XRPD pattern with absence of diffraction peaks and a FTIR spectrum with peaks at about 2940-1708-1597-1444-1380-1288-1188-1105-1033-959-880-803-678±4 cm$^{-1}$. The amorphous form of ingenol 3-(3,5-diethylisoxazole-4-carboxylate) has a Glass Transition (Tg) approximately between 60° C. and 110° C. with a maximum at about 76° C. Amorphous ingenol 3-(3,5-diethylisoxazole-4-carboxylate) is further characterized by an XRPD pattern as depicted in FIG. 1. Amorphous ingenol 3-(3,5-diethylisoxazole-4-carboxylate is further characterized by a FTIR spectrum as depicted in FIG. 2. Amorphous ingenol 3-(3,5-diethylisoxazole-4-carboxylate) is further characterized by a TG/DTA thermogram as depicted in FIG. 3. The amorphous ingenol 3-(3,5-diethylisoxazole-4-carboxylate) is prepared by dissolving ingenol 3-(3,5-diethylisoxazole-4-carboxylate) in an organic solvent, preferably dichloromethane, and quickly evaporating the organic solvent.

Another embodiment of the invention encompasses the anhydrous form of ingenol 3-(3,5-diethylisoxazole-4-carboxylate) (Form A) characterized by a XRPD pattern showing peaks at about 6.0-9.4-11.9-13.2-13.8-15.3-19.1-20.1-24.0-28.1±0.2 degrees two theta and a FTIR spectrum with peaks at about 3582-3416-2979-2940-1709-1594-1442-1380-1288-1103-1030-959-881-794-686±4 cm$^{-1}$.

Anhydrous ingenol 3-(3,5-diethylisoxazole-4-carboxylate) is further characterized by an endothermic signal in a TG/DTA analysis with maximum at about 100.5° C. and a melting peak with maximum at about 134.4° C. Anhydrous ingenol 3-(3,5-diethylisoxazole-4-carboxylate) is further characterized by an XRPD pattern as depicted in FIG. 4. Anhydrous ingenol 3-(3,5-diethylisoxazole-4-carboxylate) is further characterized by a FTIR spectrum as depicted in FIG. 5. Anhydrous ingenol 3-(3,5-diethylisoxazole-4-carboxylate is further characterized by a TG/DTA thermogram as depicted in FIG. 6. Anhydrous ingenol 3-(3,5-diethylisoxazole-4-carboxylate is further characterized by a DSC thermogram as depicted in FIG. 7. Anhydrous ingenol 3-(3,5-diethylisoxazole-4-carboxylate) is prepared by a process comprising:

a) dissolving ingenol 3-(3,5-diethylisoxazole-4-carboxylate) in methanol;
b) adding the solution to water;
c) allowing sufficient time for crystals formation;
d) separating the solid.

A further embodiment of the invention encompasses the acetone solvate of ingenol 3-(3,5-diethylisoxazole-4-carboxylate) characterized by a XRPD pattern showing peaks at about 5.7-8.5-11.4-12.1-13.1-15.4-19.1-20.6-21.6-24.0±0.2 degrees two theta and a FTIR spectrum with peaks at about 3579-3478-3364-2940-1711-1695-1595-1442-1358-1217-1105-1033-959-880-793-684±4 cm$^{-1}$. Acetone solvate of ingenol 3-(3,5-diethylisoxazole-4-carboxylate) is characterized by an endothermic signal in a TG/DTA analysis with maximum at about 123.1° C. associated with a weight loss of about 5% and a melting peak with maximum at about 134.3° C. Acetone solvate of ingenol 3-(3,5-diethylisoxazole-4-carboxylate) is further characterized by an XRPD pattern as depicted in FIG. 8. Acetone solvate of ingenol 3-(3,5-diethylisoxazole-4-carboxylate) is further characterized by a FTIR spectrum as depicted in FIG. 9. Acetone solvate of ingenol 3-(3,5-diethylisoxazole-4-carboxylate) is further characterized by a TG/DTA thermogram as depicted in FIG. 10. The acetone solvate of ingenol 3-(3,5-diethylisoxazole-4-carboxylate) is prepared by a process including the steps of: a) dissolving ingenol 3-(3,5-diethylisoxazole-4-carboxylate) in acetone
b) adding water to the solution prepared in step a
c) allowing sufficient time for crystals formation
d) separating the solid.

Another embodiment of the invention encompasses the dimethylcarbonate solvate of ingenol 3-(3,5-diethylisoxazole-4-carboxylate) characterized by a XRPD pattern showing peaks at about 5.7-8.4-10.1-11.6-13.0-14.0-15.4-19.3-21.7-23.4±0.2 degrees two theta and a FTIR spectrum with peaks at about 3581-3473-2939-1754-1709-1696-1594-1441-1287-1151-1105-1030-959-880-794-685±4 cm$^{-1}$. Dimethylcarbonate solvate of ingenol 3-(3,5-diethylisoxazole-4-carboxylate) is further characterized by a TG/DTA analysis showing an endothermic signal with maximum at about 137.0° C. associated with a weight loss of about 6-7%.

Dimethylcarbonate solvate of ingenol 3-(3,5-diethylisoxazole-4-carboxylate) is further characterized by an XRPD pattern as depicted in FIG. 11. Dimethylcarbonate solvate of ingenol 3-(3,5-diethylisoxazole-4-carboxylate) is further characterized by a FTIR spectrum as depicted in FIG. 12. Dimethylcarbonate solvate of ingenol 3-(3,5-diethylisoxazole-4-carboxylate is further characterized by a TG/DTA thermogram as depicted in FIG. 13. The dimethylcarbonate solvate of ingenol 3-(3,5-diethylisoxazole-4-carboxylate) is prepared by a process including the steps of:
a) dissolving ingenol 3-(3,5-diethylisoxazole-4-carboxylate) in dimethylcarbonate
b) allowing sufficient time for crystals formation
c) separating the solid.

Another embodiment of the invention encompasses the isopropyl ether solvate of ingenol 3-(3,5-diethylisoxazole-4-carboxylate) characterized by a XRPD pattern showing peaks at about 5.9-9.2-10.4-11.8-11.9-13.1-13.6-15.1-17.9-22.2-24.1-30.3±0.2 degrees two theta and a FTIR spectrum with peaks at about 3581-3463-2940-1705-1644-1595-1456-1442-1288-1152-1105-1029-959-881-837-794-686±4 cm$^{-1}$. Isopropyl ether solvate of ingenol 3-(3,5-diethylisoxazole-4-carboxylate) is further characterized by a TG/DTA analysis showing a weak endothermic signal below 100° C. and an endothermic peak with a maximum at about 135.7° C. associated with a weight loss of about 11.0% at 133° C. Isopropyl ether solvate of ingenol 3-(3,5-diethylisoxazole-4-carboxylate) is further characterized by an XRPD pattern as depicted in FIG. 14. Isopropyl ether solvate of ingenol 3-(3,5-diethylisoxazole-4-carboxylate) is further characterized by a FTIR spectrum as depicted in FIG. 15. Isopropyl ether solvate of ingenol 3-(3,5-diethylisoxazole-4-carboxylate) is further characterized by a TG/DTA thermogram as depicted in FIG. 16. The isopropyl ether solvate of ingenol 3-(3,5-diethylisoxazole-4-carboxylate) is prepared by a process including the steps of:
a) dissolving ingenol 3-(3,5-diethylisoxazole-4-carboxylate) in isopropyl ether
b) allowing sufficient time for crystals formation
c) separating the solid.

A further embodiment of the invention encompasses the acetonitrile solvate of ingenol 3-(3,5-diethylisoxazole-4-carboxylate) characterized FTIR spectrum with peaks at 3581-3474-3378-2940-1706-1644-1596-1456-1312-1288-1152-1104-1076-1049-1030-959-880-794-685±4 cm$^{-1}$.

Acetonitrile solvate of ingenol 3-(3,5-diethylisoxazole-4-carboxylate) is further characterized by a TG/DTA analysis showing a weak endothermic signal with maximum at about 124.4° C. associated with a weight loss of about 1.3% at 126° C.

Acetonitrile solvate of ingenol 3-(3,5-diethylisoxazole-4-carboxylate) is further characterized by an FTIR spectrum as depicted in FIG. 17.

Acetonitrile solvate of ingenol 3-(3,5-diethylisoxazole-4-carboxylate) is further characterized by a TG/DTA thermogram as depicted in FIG. 18.

The acetonitrile solvate of ingenol 3-(3,5-diethylisoxazole-4-carboxylate) is prepared by a process) including the steps of:
a) dissolving ingenol 3-(3,5-diethylisoxazole-4-carboxylate) in acetonitrile
b) allowing sufficient time for crystals formation
c) separating the solid.

A further embodiment of the invention encompasses the toluene solvate of ingenol 3-(3,5-diethylisoxazole-4-carboxylate) characterized by a XRPD pattern showing peaks at about 5.6-5.7-8.4-8.5-10.3-11.4-11.5-12.1-13.1-14.1-15.4-19.3-21.6-23.2±0.2 degrees two theta and a FTIR spectrum with peaks at about 3576-3481-2874-1706-1693-1640-1597-1497-1455-1309-1295-1106-1074-1049-1003-958-880-837-794-730-696-684-649±4 cm$^{-1}$.

Toluene solvate of ingenol 3-(3,5-diethylisoxazole-4-carboxylate) further characterized by a TG/DTA analysis showing a weak endothermic signal at a maximum at about 123.4 associated with a weight loss of about 8.4% at 129° C.

Toluene solvate of ingenol 3-(3,5-diethylisoxazole-4-carboxylate) further characterized by an XRPD pattern as depicted in FIG. 19.

Toluene solvate of ingenol 3-(3,5-diethylisoxazole-4-carboxylate) further characterized by a FTIR spectrum as depicted in FIG. 20.

Toluene solvate of ingenol 3-(3,5-diethylisoxazole-4-carboxylate) further characterized by a TG/DTA thermogram as depicted in FIG. 21.

The toluene solvate of ingenol 3-(3,5-diethylisoxazole-4-carboxylate) is prepared by a process including the steps of:
a) dissolving ingenol 3-(3,5-diethylisoxazole-4-carboxylate) in toluene
b) allowing sufficient time for crystals formation
c) separating the solid.

Another embodiment of the invention encompasses the nitromethane solvate of ingenol 3-(3,5-diethylisoxazole-4- carboxylate) characterized by a XRPD pattern showing peaks at about 5.8-8.6-9.0-10.4-11.7-13.2-14.1-15.6-21.9-23.6-24.2±0.2 degrees two theta and a FTIR spectrum with peaks at about 3579-3476-2876-1710-1643-1596-1560-1442-1358-1336-1288-1218-1105-1030-959-880-837-794-685±4 cm$^{-1}$.

Nitromethane solvate of ingenol 3-(3,5-diethylisoxazole-4-carboxylate) is further characterized by a TG/DTA analysis showing a double endothermic peak with maxima at about 125.4 and 133.9° C. associated with a weight loss of about 5.8% at 140° C.

Nitromethane solvate of ingenol 3-(3,5-diethylisoxazole-4-carboxylate) is further characterized by an XRPD pattern as depicted in FIG. 22.

Nitromethane solvate of ingenol 3-(3,5-diethylisoxazole-4-carboxylate) is further characterized by a FTIR spectrum as depicted in FIG. 23.

Nitromethane solvate of ingenol 3-(3,5-diethylisoxazole-4-carboxylate) is further characterized by a TG/DTA thermogram as depicted in FIG. 24.

The nitromethane solvate of ingenol 3-(3,5-diethylisoxazole-4-carboxylate) is prepared by a process including the steps of:

a) dissolving ingenol 3-(3,5-diethylisoxazole-4-carboxylate) in nitromethane b) allowing sufficient time for crystals formation c) separating the solid.

A further embodiment of the invention encompasses the mesitylene solvate of ingenol 3-(3,5-diethylisoxazole-4-carboxylate) characterized by data selected from the group consisting of: a XRPD pattern showing peaks at about 5.3-6.0-9.1-10.5-12.1-13.0-14.8-18.2-22.3-24.3-25.8-28.6-30.6-34.7±0.2 degrees two theta and a FTIR spectrum with peaks at about 3580-3479-2876-1705-1642-1595-1560-1455-1441-1381-1311-1288-1150-1105-1074-1029-1003-958-880-836-794-685±4 cm$^{-1}$. Mesitylene solvate of ingenol 3-(3,5-diethylisoxazole-4-carboxylate) is further characterized by a TG/DTA analysis showing an endothermic peak with maximum at about 133.2° C. associated with a weight loss of about 2.0% at 131° C. Mesitylene solvate of ingenol 3-(3,5-diethylisoxazole-4-carboxylate) is further characterized by an XRPD pattern as depicted in FIG. 25. Mesitylene solvate of ingenol 3-(3,5-diethylisoxazole-4-carboxylate) further characterized by a FTIR spectrum as depicted in FIG. 26. Mesitylene solvate of ingenol 3-(3,5-diethylisoxazole-4-carboxylate) further characterized by a TG/DTA thermogram as depicted in FIG. 27. The mesitylene solvate of ingenol 3-(3,5-diethylisoxazole-4-carboxylate) is prepared by a process including the steps of:

a) dissolving ingenol 3-(3,5-diethylisoxazole-4-carboxylate) in mesitylene b) allowing sufficient time for crystals formation c) separating the solid.

Another embodiment of the invention encompasses the dichloromethane/heptane solvate of ingenol 3-(3,5-diethylisoxazole-4-carboxylate) characterized by a XRPD pattern showing peaks at about 5.7-8.6-9.0-10.4-11.6-12.2-12.9-14.4-15.5-17.5-19.9-21.7-22.4-28.1-29.4±0.2 degrees two theta and a FTIR spectrum with peaks at about 3578-3474-2876-1705-1652-1596-1454-1442-1288-1217-1152-1105-1075-1050-1030-1003-958-880-837-794-770-739-700-685±4 cm$^{-1}$.

Dichloromethane/heptane solvate of ingenol 3-(3,5-diethylisoxazole-4-carboxylate) is further characterized by a TG/DTA analysis showing an endothermic signal with maximum at about 130.7° C. associated with a weight loss of about 4.1% between 130 and 135° C.

Dichloromethane/heptane solvate of ingenol 3-(3,5-diethylisoxazole-4-carboxylate) is further characterized by an XRPD pattern as depicted in FIG. 28.

Dichloromethane/heptane solvate of ingenol 3-(3,5-diethylisoxazole-4-carboxylate) is further characterized by a FTIR spectrum as depicted in FIG. 29.

Dichloromethane/heptane solvate of ingenol 3-(3,5-diethylisoxazole-4-carboxylate) further characterized by a TG/DTA thermogram as depicted in FIG. 30.

The dichloromethane/heptane solvate of ingenol 3-(3,5-diethylisoxazole-4-carboxylate) is prepared by a process including the steps of:

a) dissolving ingenol 3-(3,5-diethylisoxazole-4-carboxylate) in dichloromethane b) adding heptane c) allowing sufficient time for crystals formation d) separating the solid.

Another embodiment of the invention encompasses the ethyl acetate solvate of ingenol 3-(3,5-diethylisoxazole-4-carboxylate) characterized by a XRPD pattern showing peaks at about 5.8-8.6-10.0-11.6-12.7-13.1-14.0-15.6-16.0-19.1-20.2-22.0-23.2±0.2 degrees two theta.

Ethyl acetate solvate of ingenol 3-(3,5-diethylisoxazole-4-carboxylate) is further characterized by TG/DTA analysis showing an endothermic signal with maximum at about 123.8° C. associated with a weight loss of about 5.4% at about 130° C.

Ethyl acetate solvate of ingenol 3-(3,5-diethylisoxazole-4-carboxylate) is further characterized by an XRPD pattern as depicted in FIG. 31.

Ethyl acetate solvate of ingenol 3-(3,5-diethylisoxazole-4-carboxylate is further characterized by a TG/DTA thermogram as depicted in FIG. 32.

The ethyl acetate solvate of ingenol 3-(3,5-diethylisoxazole-4-carboxylate) is prepared by a process including the steps of:

a) dissolving ingenol 3-(3,5-diethylisoxazole-4-carboxylate) in ethyl acetate b) allowing sufficient time for crystals formation c) separating the solid.

EXAMPLES

Thermal Analysis: Thermogravimetry and Differential Thermal Analysis (TG-DTA)

The analyses were performed using a Seiko TG/DTA7200 simultaneous system using open aluminum pans (40 μl volume). The TG/DT signals were recorded from 30 to 250° C. with linear heating rate (10° C./min) under a 200 ml/min nitrogen flow. About 10 mg of powder was used for each measurement. The thermal profiles were acquired and elaborated by Seiko MUSE Software.

X-Ray Powder Diffractometry (XRPD)

The diffraction pattern was recorded with a Bruker D2-Phaser diffractometer.

Tube anode: Cu

Generator tension (kV): 30

Generator current (mA): 10

Wavelengths λ1 and λ2 (Å): 1.54056, 1.54439

Intensity ratio (λ2/λ1): 0.500

Spinner: off

Angular range (2θ°): 2.00-50.00

Step size (2θ°): 0.020

Time per step (sec): 3.0

Fourier-Transform InfraRed Spectroscopy (FTIR)

The infrared spectra were recorded in Attenuated Total Reflectance (ATR) mode using Fourier-Transform spectrometer Perkin Elmer Spectrum One, equipped with Specac ATR Golden Gate and Spectrum ES software (Perkin Elmer). The spectra were the result of the acquisition and transformation of 16 co-added scans in the 4000-550 cm$^{-1}$ spectral region at a resolution of 4 cm$^{-1}$.

Example 1 (Amorphous)

Ingenol 3-(3,5-diethylisoxazole-4-carboxylate) (2.0 g) was dissolved in Dichloromethane (26.5 mL) at 20-25° C. The solvent was rapidly removed under vacuum using a rotoevaporator. Amorphous Ingenol 3-(3,5-diethylisoxazole-4-carboxylate) was obtained as a white solid (2.0 g).

Example 2 (Anhydrous)

Ingenol 3-(3,5-diethylisoxazole-4-carboxylate) (5.0 g) was dissolved in methanol (26.5 mL) at 20-25° C. and added dropwise to water (530 mL). The solution was left to crystallize overnight at 20-25° C. The solid was filtered, washed with a MeOH/water 1:20 and dried at 50° C. for 40 hours. Anhydrous Ingenol 3-(3,5-diethylisoxazole-4-carboxylate) was obtained as a white powder (4.8 g).

Example 3 (Acetone Solvate)

Ingenol 3-(3,5-diethylisoxazole-4-carboxylate) (6.3 g) was dissolved in acetone (32 mL) at 20-25° C. Water was added dropwise until the haze formation. Crystals were allowed to grow for 1 hour and further water was added dropwise for a total of 32 mL. The suspension was stirred overnight at 20-25° C. The solid was filtered, washed with acetone:water 1:1 (10 mL) and dried overnight at 50° C. The acetone solvate of Ingenol 3-(3,5-diethylisoxazole-4-carboxylate) was obtained as a white powder (5.6 g).

Example 4 (Dimethylcarbonate Solvate)

Ingenol 3-(3,5-diethylisoxazole-4-carboxylate) (100 mg) was dissolved in dimethylcarbonate (0.5 mL) at 20-25° C. The crystallization started immediately after dissolution. The mixture was stirred for 72 hours, filtered and washed with dimethylcarbonate. The dimethylcarbonate solvate of Ingenol 3-(3,5-diethylisoxazole-4-carboxylate) was obtained as a white powder (85 mg).

Example 5 (Isopropyl Ether Solvate)

Ingenol 3-(3,5-diethylisoxazole-4-carboxylate) (100 mg) was dissolved in isopropyl ether (0.5 mL) at 20-25° C. The crystallization started after 30 minutes. The mixture was stirred for 72 hours, filtered and washed with isopropyl ether. The isopropyl ether solvate of Ingenol 3-(3,5-diethylisoxazole-4-carboxylate) was obtained as a white powder (80 mg).

Example 6 (Acetonitrile Solvate)

Ingenol 3-(3,5-diethylisoxazole-4-carboxylate) (100 mg) was dissolved in acetonitrile (0.5 mL) at 20-25° C. The mixture was stirred for 72 hours, filtered and washed with acetonitrile. The acetonitrile solvate of Ingenol 3-(3,5-diethylisoxazole-4-carboxylate) was obtained as a white powder (87 mg).

Example 7 (Toluene Solvate)

Ingenol 3-(3,5-diethylisoxazole-4-carboxylate) (100 mg) was dissolved in toluene (0.5 mL) at 20-25° C. The mixture was stirred for 72 hours, filtered, washed with toluene and dried under vacuum for 24 hours at 50° C. The toluene solvate of Ingenol 3-(3,5-diethylisoxazole-4-carboxylate) was obtained as a white powder (91 mg).

Example 8 (Nitromethane Solvate)

Ingenol 3-(3,5-diethylisoxazole-4-carboxylate) (100 mg) was dissolved in nitromethane (0.5 mL) at 20-25° C. The mixture was stirred for 72 hours, filtered and washed with nitromethane. The nitromethane solvate of Ingenol 3-(3,5-diethylisoxazole-4-carboxylate) was obtained as a white powder (82 mg).

Example 9 (Mesitylene Solvate)

Ingenol 3-(3,5-diethylisoxazole-4-carboxylate) (100 mg) was dissolved in mesitylene (0.5 mL) at 20-25° C. The mixture was stirred for 72 hours, filtered, washed with mesitylene and dried under vacuum for 24 hours at 50° C. The mesitylene solvate of Ingenol 3-(3,5-diethylisoxazole-4-carboxylate) was obtained as a white powder (88 mg).

Example 10 (Ethyl Acetate Solvate)

Ingenol 3-(3,5-diethylisoxazole-4-carboxylate) (100 mg) was dissolved in ethyl acetate (0.5 mL) at 20-25° C. The mixture was stirred for 72 hours, filtered, washed with ethyl acetate and dried under vacuum for 24 hours at 50° C. The ethyl acetate solvate of Ingenol 3-(3,5-diethylisoxazole-4-carboxylate) was obtained as a white powder (91 mg).

The invention claimed is:

1. A solid form of ingenol 3-(3,5-diethylisoxazole-4-carboxylate) selected from the group consisting of an amorphous form and a crystalline anhydrous form;
   wherein the amorphous form is characterized by a XRPD pattern showing absence of diffraction peaks, a FTIR spectrum having peaks at about 2940-1708-1597-1444-1380-1288-1188-1105-1033-959-880-803-678±4 cm$^{-1}$ and by a Glass Transition (Tg) approximately between 60° C. and 110° C. with a maximum at about 76° C.; and
   wherein the crystalline anhydrous form is characterized by a XRPD pattern showing peaks at about 6.0-9.4-11.9-13.2-13.8-15.3-19.1-20.1-24.0-28.1±0.2 degrees two theta, a FTIR pattern with peaks at about 3582-3416-2979-2940-1709-1594-1442-1380-1288-1103-1030-959-881-794-686±4 cm$^{-1}$ and by a TG/DTA thermogram showing an endothermic signal with maximum at about 100.5° C. and a melting peak with maximum at about 134.4° C.

2. The solid form of ingenol 3-(3,5-diethylisoxazole-4-carboxylate) according to claim 1, which is said amorphous form.

3. The solid form of ingenol 3-(3,5-diethylisoxazole-4-carboxylate) according to claim 1, which is said crystalline anhydrous form.

4. A solid solvate of ingenol 3-(3,5-diethylisoxazole-4-carboxylate) selected from the group consisting of an acetone solvate, a dimethylcarbonate solvate, an isopropyl ether solvate, an acetonitrile solvate, a toluene solvate, a mesitylene solvate, a nitromethane solvate, a dichloromethane/heptane solvate and an ethyl acetate solvate;
   wherein the acetone solvate characterized by a XRPD pattern showing peaks at about 5.7-8.5-11.4-12.1-13.1-15.4-19.1-20.6-21.6-24.0±0.2 degrees two theta, by a FTIR pattern with peaks at about 3579-3478-3364-

2940-1711-1695-1595-1442-1358-1217-1105-1033-959-880-793-684±4 cm$^{-1}$ and by a TG/DTA thermogram showing an endothermic signal with maximum at about 123.1° C. associated with a weight loss of about 5% and a melting peak with maximum at about 134.3° C.;

wherein the dimethylcarbonate solvate is characterized by a XRPD pattern showing peaks at about 5.7-8.4-10.1-11.6-13.0-14.0-15.4-19.3-21.7-23.4±0.2 degrees two theta, by a FTIR pattern with peaks at about 3581-3473-2939-1754-1709-1696-1594-1441-1287-1151-1105-1030-959-880-794-685±4 cm$^{-1}$ and by a TG/DTA thermogram showing an endothermic signal with maximum at about 137.0° C. associated with a weight loss of about 6-7%;

wherein the isopropyl ether solvate is characterized by a XRPD pattern showing peaks at about 5.9-9.2-10.4-11.8-11.9-13.1-13.6-15.1-17.9-22.2-24.1-30.3±0.2 degrees two theta, by a FTIR pattern with peaks at about 3581-3463-2940-1705-1644-1595-1456-1442-1288-1152-1105-1029-959-881-837-794-686±4 cm$^{-1}$ and by a TG/DTA thermogram showing a weak endothermic signal below 100° C. and an endothermic peak with a maximum at about 135.7° C. associated with a weight loss of about 11.0% at 133° C.;

wherein the acetonitrile solvate is characterized by FTIR spectrum with peaks at 3581-3474-3378-2940-1706-1644-1596-1456-1312-1288-1152-1104-1076-1049-1030-959-880-794-685±4 cm$^{-1}$ and by a TG/DTA thermogram showing a weak endothermic signal with maximum at about 124.4° C. associated with a weight loss of about 1.3% at 126° C.;

wherein the toluene solvate is characterized by a XRPD pattern showing peaks at about 5.6-5.7-8.4-8.5-10.3-11.4-11.5-12.1-13.1-14.1-15.4-19.3-21.6-23.2±0.2 degrees two theta, by a FTIR pattern with peaks at about 3576-3481-2874-1706-1693-1640-1597-1497-1455-1309-1295-1106-1074-1049-1003-958-880-837-794-730-696-684-649±4 cm$^{-1}$ and by a weak endothermic signal at a maximum at about 123.4 associated with a weight loss of about 8.4% at 129° C.;

wherein the nitromethane solvate is characterized by a XRPD pattern showing peaks at about 5.8-8.6-9.0-10.4-11.7-13.2-14.1-15.6-21.9-23.6-24.2±0.2 degrees two theta, by a FTIR pattern with peaks at about 3579-3476-2876-1710-1643-1596-1560-1442-1358-1336-1288-1218-1105-1030-959-880-837-794-685±4 cm$^{-1}$ and by a TG/DTA thermogram showing a double endothermic peak with maxima at about 125.4 and 133.9 associated with a weight loss of about 5.8% at 140° C.;

wherein the mesitylene solvate is characterized by a XRPD pattern showing peaks at about 5.3-6.0-9.1-10.5-12.1-13.0-14.8-18.2-22.3-24.3-25.8-28.6-30.6-34.7±0.2 degrees two theta, a FTIR spectrum with peaks at about 3580-3479-2876-1705-1642-1595-1560-1455-1441-1381-1311-1288-1150-1105-1074-1029-1003-958-880-836-794-685±4 cm$^{-1}$ and by a TG/DTA thermogram showing an endothermic peak with maximum at about 133.2° C. associated with a weight loss of about 2.0% at 131° C.;

wherein the dichloromethane/heptane solvate is characterized by a XRPD pattern showing peaks at about 5.7-8.6-9.0-10.4-11.6-12.2-12.9-14.4-15.5-17.5-19.9-21.7-22.4-28.1-29.4±0.2 degrees two theta, by a FTIR spectrum with peaks at about 3578-3474-2876-1705-1652-1596-1454-1442-1288-1217-1152-1105-1075-1050-1030-1003-958-880-837-794-770-739-700-685±4 cm$^{-1}$ and by an endothermic signal with maximum at about 130.7° C. associated with a weight loss of about 4.1% between 130 and 135° C.; and wherein the ethyl acetate solvate is characterized by a XRPD pattern showing peaks at about 5.8-8.6-10.0-11.6-12.7-13.1-14.0-15.6-16.0-19.1-20.2-22.0-23.2±0.2 degrees two theta and by a TG/DTA thermogram showing an endothermic signal with maximum at about 123.8° C. associated with a weight loss of about 5.4% at about 130° C.

5. The solid solvate of ingenol 3-(3,5-diethylisoxazole-4-carboxylate) according to claim 4, which is said acetone solvate.

6. The solid solvate of ingenol 3-(3,5-diethylisoxazole-4-carboxylate) according to claim 4, which is said dimethylcarbonate solvate.

7. The solid solvate of ingenol 3-(3,5-diethylisoxazole-4-carboxylate) according to claim 4, which is said isopropyl ether solvate.

8. The solid solvate of ingenol 3-(3,5-diethylisoxazole-4-carboxylate) according to claim 4, which is said acetonitrile solvate.

9. The solid solvate of ingenol 3-(3,5-diethylisoxazole-4-carboxylate) according to claim 4, which is said toluene solvate.

10. The solid solvate of ingenol 3-(3,5-diethylisoxazole-4-carboxylate) according to claim 4, which is said nitromethane solvate.

11. The solid solvate of ingenol 3-(3,5-diethylisoxazole-4-carboxylate) according to claim 4, which is said mesitylene solvate.

12. The solid solvate of ingenol 3-(3,5-diethylisoxazole-4-carboxylate) according to claim 4, which is said dichloromethane/heptane solvate.

13. The solid solvate of ingenol 3-(3,5-diethylisoxazole-4-carboxylate) according to claim 4, which is said ethyl acetate solvate.

* * * * *